United States Patent
Martin

(10) Patent No.: US 7,582,758 B2
(45) Date of Patent: Sep. 1, 2009

(54) LEWIS ACID MEDIATED SYNTHESIS OF CYCLIC ESTERS

(75) Inventor: Kevin V. Martin, Solana Beach, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 527 days.

(21) Appl. No.: 11/144,348

(22) Filed: Jun. 3, 2005

(65) Prior Publication Data

US 2005/0282782 A1 Dec. 22, 2005

Related U.S. Application Data

(60) Provisional application No. 60/578,467, filed on Jun. 8, 2004.

(51) Int. Cl.
*C07D 473/00* (2006.01)
(52) U.S. Cl. ........................ 544/276; 544/277
(58) Field of Classification Search ............... 546/153, 546/159, 160; 544/276, 277
See application file for complete search history.

(56) References Cited

U.S. PATENT DOCUMENTS

| | | | |
|---|---|---|---|
| 3,018,302 A | 1/1962 | Bielefeld et al. | |
| 4,590,269 A * | 5/1986 | Prisbe et al. | 544/244 |
| 4,659,825 A | 4/1987 | Holy et al. | |
| 4,724,233 A | 2/1988 | De Clercq et al. | |
| 4,808,716 A | 2/1989 | Hol et al. | |
| 4,952,740 A | 8/1990 | Juge et al. | |
| 5,130,427 A | 7/1992 | Alexander et al. | |
| 5,142,051 A | 8/1992 | Holy et al. | |
| 5,157,027 A | 10/1992 | Biller et al. | |
| 5,514,798 A | 5/1996 | Bichofberger et al. | |
| 5,658,889 A | 8/1997 | Gruber et al. | |
| 5,663,159 A | 9/1997 | Starrett, Jr. et al. | |
| 5,665,386 A | 9/1997 | Benet et al. | |
| 5,686,629 A | 11/1997 | Bichofberger et al. | |
| 5,716,928 A | 2/1998 | Benet et al. | |
| 5,962,440 A | 10/1999 | Sulsky | |
| 5,962,522 A | 10/1999 | Wacher et al. | |
| 6,004,927 A | 12/1999 | Benet et al. | |
| 6,028,054 A | 2/2000 | Benet et al. | |
| 6,037,335 A | 3/2000 | Takashima et al. | |
| 6,054,587 A | 4/2000 | Reddy et al. | |
| 6,110,903 A | 8/2000 | Kasibhatla et al. | |
| 6,121,234 A | 9/2000 | Benet et al. | |
| 6,180,666 B1 | 1/2001 | Wacher et al. | |
| 6,284,748 B1 | 9/2001 | Dang et al. | |
| 6,294,672 B1 | 9/2001 | Reddy et al. | |
| 6,312,662 B1 * | 11/2001 | Erion et al. | 424/9.1 |
| 6,399,782 B1 | 6/2002 | Kasibhatla et al. | |
| 6,489,476 B1 | 12/2002 | Dang et al. | |
| 6,752,981 B1 | 6/2004 | Erion et al. | |
| 6,946,115 B2 | 9/2005 | Erion et al. | |
| 2003/0225277 A1 | 12/2003 | Kopcho et al. | |
| 2003/0229225 A1 | 12/2003 | Reddy et al. | |
| 2004/0092476 A1 | 5/2004 | Boyer et al. | |
| 2004/0192651 A1 | 9/2004 | Reddy et al. | |
| 2005/0288240 A1 | 12/2005 | Erion et al. | |
| 2006/0030545 A1 | 2/2006 | Cheng et al. | |
| 2006/0046981 A1 | 3/2006 | Shibata | |

FOREIGN PATENT DOCUMENTS

| | | |
|---|---|---|
| EP | 0161955 A1 | 11/1985 |
| EP | 0180276 A1 | 5/1986 |
| EP | 0338372 A2 | 10/1989 |
| EP | 0353692 B1 | 10/1995 |
| EP | 0481214 B1 | 6/1998 |
| EP | 0632048 B1 | 3/2001 |
| WO | WO 91/19721 A1 | 12/1991 |
| WO | WO 93/19075 A1 | 9/1993 |
| WO | WO 95/07920 A1 | 3/1995 |
| WO | WO 96/01267 A1 | 1/1996 |
| WO | WO 97/03679 A1 | 2/1997 |
| WO | WO 98/39342 A1 | 9/1998 |
| WO | WO 98/39343 A1 | 9/1998 |
| WO | WO 98/39344 A1 | 9/1998 |
| WO | WO 99/04774 A2 | 2/1999 |
| WO | WO 99/45016 A2 | 9/1999 |
| WO | WO9945016 * | 9/1999 |
| WO | WO 00/52015 A2 | 9/2000 |
| WO | WO 01/18013 A1 | 3/2001 |
| WO | WO 02/08241 A2 | 1/2002 |
| WO | WO 03/095665 A2 | 11/2003 |
| WO | WO 2004/037161 A2 | 5/2004 |
| WO | WO 2004/041834 A2 | 5/2004 |
| WO | WO 2004/041837 A1 | 5/2004 |

OTHER PUBLICATIONS

Jones, Organic Letters, vol. 4(21), pp. 3671-3673, 2002.*

Bijsterbosch et al., "Disposition of the Acyclic Nucleoside Phosphonate (S)-9-(3-Hydroxy-2-Phosphonuylmethoxypropyl)Adenine", Antimicrob. Agents Chemother., 42(5):1146-50 (1998).

(Continued)

*Primary Examiner*—D. Margaret Seaman
(74) *Attorney, Agent, or Firm*—Arnold & Porter LLP

(57) ABSTRACT

Methods for the synthesis of cyclic phosphonic acid diesters from 1,3-diols are described, whereby cyclic phosphonic acid diesters are produced by reacting a chiral 1,3-diol and an activated phosphonic acid in the presence of a Lewis acid.

39 Claims, No Drawings

OTHER PUBLICATIONS

Farquhar et al., "Biologically Reversible Phosphate-Protective Groups", J. Pharm. Sci. 72:324 (1983).

Krise, D.P and V.J. Stellar, "Prodrugs of phosphates, phosphonates, and phosphinates", Adv. Drug. Del. Rev. 19:287 (1996).

Prisbe et al., "Synthesis and Antiherpes Virus Activity of Phosphate and Phosphonate Derivatives of 9-[(1,3-Dihydroxy-2-propoxy)methyl]guanine", J. Med. Chem. 29: 671 (1986).

Ozoe et al., "Actions of cyclic esters, S-esters, and amides of phenyl- and phenylthiophosphonic acids on mammalia and insect GABA-gated chloride channels", Bioorg. Med. Chem. 6:73 (1998).

Evans et al., "New Procedure for the Direct Generation of Titanium Enolates. Diastereoselective Bond Constructions with Representative Electrophiles", J. Am. Chem. Soc. 112:8215 (1998).

Evans et al., "Stereoselective Aldol Reactions of Cholrotitanium Enolates. An Efficient Method fo the ASsemblage of Polypropionate-Related Synthons", J. Am. Chem. Soc. 113:1047 (1991).

Jones et al., "A Simple and Effective Method for Phosphoryl Transfer Using TiCl4 Catalysis" Org. Lett. 4(21):3671 (2002).

Alexander, P. et al. "Preparation of 9-(2-Phosphonomethoxyethyl) Adenine Esters as Potential Prodrugs" Collect. Czech. Chem. Commun. 59, 1853-1869 (1994).

Ambhaikar, N.B., et al., "Diastereoselective Addition of Cholorotitanium Enolate of N-Acyl Thiazolidinethione to O-Methyl Oximes: A Novel, Stereoselective Synthesis of α,β-Distributed β-Amino Carbonyl Compounds via Chiral Auxiliary Mediated Azetine Formation," J. Am. Chem. Soc., vol. 125, 3690-3691, American Chemical Society (2003).

Amin, D., et al., "1-Hydroxy-3-(methylpentylamino)-propylidene-1,1-bisphosphonic Acid as a Potent Inhibitor of Squalene Synthase," Arzneim.-Forsch/Drug Res. 46:759-762, Blackwell Publishing, Inc. (1996).

Atiq, O., et al., "Treatment of Unresectable Primary Liver Cancer with Intrahepatic Fluorodeoxyuridine and Mitomycin C Through an Implantable Pump," Cancer 69:920-924, John Wiley and Sons, Inc. (1992).

Auberson, Y., et al., "N-Phosphonoalkyl-5-Aminomethylquinoxaline-2,3-Diones: In Vivo Active AMPA and NMDA-(Glycine) Antagonists," Bioorg. Med. Chem. Lett. 9:249-254, Elsevier Science Ltd. (1999).

Balthazor, T. and Grabiak, R.C., "Nickel-Catalyzed Arbuzov Reaction: Mechanistic Observations," J. Org. Chem. 45:5425-5426, American Chemical Society (1980).

Balzarini, J. et al., "Activity of the (R)-Enantiomers of 9-(2-Phosphonylmethoxypropyl)-Adenine and 9-(2-Phosphonylmethoxypropyl)-2,6-diamiopurine against Human Immunodeficiency Virus in Different Human Cell Systems" Biochem. and Biophys. Res. Commun. 219:337-341, Academic Press, Inc. (1996).

Barluenga, José, et al., "Reduction of 1,3-Diimines. A New and General Method of Synthesis of γ-Diamines, β-Amino Ketones, and Derivatives with Two and Three Chiral Centers" J. Org. Chem. 48:2255-2259, American Chemical Society (1983).

Barragán, E., et al., "Stereoselective Addition of the Titanium Enolate of N-Acetyl (4S)-Isopropyl-1,3-thiazolidine-2-thione to Five-Membered N-Acyl Iminium Ions," J. Org. Chem., vol. 70, 4214-4217, American Chemical Society (2005).

Basavaiah, D., et al., "Steric Factors Direct Baylis-Hillman and Aldol Reactions in Titanium Tetrachloride Mediated Coupling between α-Keto Esters and Cyclohex-2-enone Derivatives," J. Org. Chem., vol. 68, 5983-5991, American Chemical Society (2003).

Beaucage, S.L. and Iyer, R.P., "The Synthesis of Modified Oligonucleotides by the Phosphoramidite Approach and Their Applications," Tetrahedron 49:6123-6194, Pergamon Press Ltd. (1993).

Belokon, Y.N., et al., "Catalytic Asymmetric Synthesis of O-Acetylcyanohydrins from Potassium Cyanide, Acetic Anhydride, and Aldehydes, Promoted by Chiral Salen Complexes of Titanium(IV) and Vanadium(V)," Helvetica Chimica Acta, vol. 85, 3301-3312 (2002).

Belokon, Y.N., et al., "The Asymmetric Addition of Trimethylsilyl Cyanide to Aldehydes Catalyzed by Chiral (Salen) Titanium Complexes," J. Am. Chem. Soc., vol. 121, 3968-3973, American Chemical Society (1999).

Benhamou, Y., et al., "Safety and Efficacy of Adefovir Dipivoxil in Patients Co-infected with HIV-1 and Lamivudine-resistant Hepatitis B Virus: an Open-label Pilot Study," The Lancet, vol. 358, 718-723, The Lancet Publish. Group (2001).

Benzaria, S., et al., "Synthesis, in Vitro Antiviral Evaluation, and Stability Studies of Bis(S-acyl-2-thioethyl) Ester Derivatives of 9-[2-(Phosphonomethoxy)ethyl]adenine (PMEA) as Potential PMEA Prodrugs with Improved Oral Bioavailability," J. Med. Chem., vol. 39, 4958-4965, American Chemical Society (1996).

Berry, M.N. and Friend, D.S., "High-Yield Preparation of Isolated Rat Liver Parenchymal Cells. A Biochemical and Fine Structural Study," J. Cell Biol. 43:506-520, Rockefeller University Press (1969).

Bespalov, A., et al., "Prolongation of morphine analgesia by competitive NMDA receptor antagonist D-CPPene (SDZ EAA 494) in rats," Eur. J. Pharmacol. 351:299-305, Elsevier Science B.V. (1998).

Bhongle, N.N., et al., "Expedient and High-Yield Synthesis of Alkylphosphonyl Dichlorides Under Mild, Neutral Conditions: Reaction of Bis(Trimethylsilyl) Alkyl Phosphonates with Oxalyl Chloride/Dimethylformamide," Synthetic Comm. 17:1071-1076, Marcel Dekker, Inc. (1987).

Bird, J., et al., "Synthesis of Novel N-Phosphonoalkyl Dipeptide Inhibitors of Human Collagenase," J. Med. Chem. 37:158-169, American Chemical Society (1994).

Borch, R.F. and Millard, J.A., "The Mechanism of Activation of 4-Hydroxycyclophosphamide," J. Med. Chem. 30:427-431, American Chemical Society (1987).

Brill, T. and Landon, S.J., "Arbuzov-like Dealkylation Reactions of Transition-Metal-Phosphite Complexes," Chem. Rev. 84:577-585, American Chemical Society (1984).

Bronson, J.J., et al., "Synthesis and Antiviral Activity of Phosphonylmethoxyethyl Derivatives of Purine and Pyrimidine Bases," in Nucleotide Analogues as Antiviral Agents, ACS Symposium Series 401, pp. 72-87, American Chemical Society (1989).

Bronson, J.J., et al., "Synthesis and Antiviral Activity of Nucleotide Analogues Bearing the (S)-(3-Hydroxy-2-phosphonylmethoxy)propyl Moiety Attached to Adenine, Guanine, and Cytosine," in Nucleotide Analogues as Antiviral Agents, ACS Symposium Series 401, pp. 88-102, American Chemical Society (1989).

Campagne, J. et al. "Synthesis of Mixed Phosphate Diester Analogues of Dipeptides using BOP or PyBOP Reagents" Tetrahedron Lett. 34(42), 6743-6744 (1993).

Campbell, D. "The Synthesis of Phosphonate Esters, and Extension of the Mitsunobu Reation" J. Org. Chem. 57, 6331-6335 (1992).

Cardellicchio, C., et al., "A Convenient Route to the Phosphorus and Sulfur Stereoisomers of Ethyl Menthyl (Methylsulfinyl)methylphosphonate," Tetrahedron: Asymmetry, vol. 15, 1471-1476, Elsevier Ltd. (2004).

Casara, P. et al. "Synthesis of Acid Stable 5'-O-Fluoromethyl Phosphonates of Nucleosides. Evaluation as Inhibitors of Reverse Transcriptase" Bioorg. Med. Chem. Lett. 2(2), 145-148 (1992).

Casper, D.M., et al., "An Improved Procedure for the Asymmetric Aldol Reaction of the Titanium enolate of an N3-Propionyl-3,4,5,6-tetrahydro-2H-1,3,4-oxadiazin-2-one," Tetrahedron: Asymmetry, vol. 14, 517-521, Elsevier Ltd. (2003).

Casper, D.M., et al., "Toward the Development of a Structurally Novel Class of Chiral Auxiliaries: Diastereoselective Aldol Reactions of a (1R,2S)-Ephedrine-Based 3,4,5,6-Tetrahydro-2H-1,3,4-oxadiazin-2-one," Organic Letters, vol. 4, No. 21, 3739-3742, American Chemical Society (2002).

Casteel, D. and Peri, S.P., "Steric and Electronic Effects in the Aryl Phosphate to Arylphosphonate Rearrangement," Synthesis (9):691-693, Georg Thieme Verlag KG (1991).

Chen, L. and Waxman, D.J., "Intratumoral Activation and Enhanced Chemotherapeutic Effect of Oxazaphosphorines following Cytochrome P-450 Gene Transfer: Development of a Combined Chemotherapy/Cancer Gene Therapy Strategy," Cancer Res. 55:581-589, The American Association for Cancer Research (1995).

Chen, L., et al., "Sensitization of Human Breast Cancer Cells to Cyclophosphamide and Ifosfamide by Transfer of a Liver Cytochrome P450 Gene," *Cancer Res.* 56:1331-1340, The American Association for Cancer Research (1996).

Chu, Daniel T.W. "A Regiospecific Synthesis of 1-Methylamino-6-fluoro-7-(4-methylpiperazin-l-yl)-1,4-dihydro-4-oxoquinoline-3-carboxylic Acid" *J. Heterocyclic Chem.* 22:1033-1034 (1985).

Chu, C.K. et al. "Chemistry and Antiviral Activities of Acyclonucleosides" *J. Heterocyclic Chem.* 23:289-319 (1986).

Clerici, A., et al., "Reactivity of Methyl Mandelate-Ti(IV)-enediolate: Oxidative Homocoupling versus Aldol and DirectMannich-Type *Syn*-Diastereoselective Condensation," *J. Org. Chem.*, vol. 70, 4174-4176, American Chemical Society (2005).

Cooper, D.B., et al., "Use of Carbohydrate Derivatives for Studies of Phosphorus Stereo-chemistry. Part II. Synthesis and Configurational Assignments of 1,-3,2-Oxathiaphosphorinan-2-ones and 1,3,2-Dioxaphosphorinan-2-thiones," *J. Chem. Soc. Perkin I* 3/2422:1049-1052, Royal Society of Chemistry (1974).

Coppi, L., et al., "Lewis Acid Mediated Condensation of Alkenols and Aldehydes. A Selective Synthesis of Tetrahydropyrans and Oxepanes," *J. Org. Chem.*, vol. 53, 911-913, American Chemical Society (1988).

Crimmins, M.T. and Choy, A., "An Asymmetric Aldol-Ring-Closing Metathesis Strategy for the Enantioselective Construction of Oxygen Heterocycles: an Efficient Approach to the Enantioselective Synthesis of (+)-Laurencin," *J. Am. Chem. Soc.* 121:5653-5660, American Chemical Society (1999).

Crimmins, M.T., et al., "Anti-Selective Aldol Reactions with Titanium Enolates of *N*-Glycoolyloxazolidinethiones," *Organic Letters*, vol. 5, No. 4, 591-594, American Chemical Society (2003).

Cundy, K.C., et al., "Clinical Pharmacokinetics of the Antiviral Nucleotide Analogues Cidofovir and Adefovir," *Clin. Pharmacokinet.*, vol. 36(2), 127-143 (1999).

Cundy, K.C., et al., "Oral Formulations of Adefovir Dipivoxil: In Vitro Dissolution and In Vivo Bioavailability in Dogs," *Journal of Pharmaceutical Sciences*, vol. 86, No. 12, 1334-1338, American Chemical Society and American Pharmaceutical Association (1997).

Dang, Q. et al., "A New Regio-Defined Synthesis of PMEA" *Nucleosides & Nucleotides* 17/8: 1445-1451, Marcel Dekker, Inc. (1998).

Dearfield, K., et al., "Analysis of the genotoxicity of nine acrylate/methacrylate compounds in L5178Y mouse lymphoma cells," *Mutagenesis* 4:381-393, Oxford University Press (1989).

De Clercq, E., et al., "A novel selective broad-spectrum anti-DNA virus agent," *Nature* 323:464-467, Nature Publishing Group (1986).

De Clercq, E., et al., "Antiviral Activity of Phosphonylmethoxyalkyl Derivatives of Purine and Pyrimidines," *Antiviral Research*, vol. 8, 261-272, Elsevier Science Publishers B.V. (1987).

De Lombaert, S., et al., "Pharmacological Profile of a Non-Peptidic Dual Inhibitor of Neutral Endopeptidase 24.11 and Endothelin-Converting Enzyme," *Biochem. Biophys. Res. Commun.* 204:407-412, Academic Press, Inc. (1994).

De Lombaert, S., et al., "*N*-Phosphomomethyl Dipeptides and Their Phosphonate Prodrugs a New Generation of Neutral Endopeptidase (NEP, EC 3.4.24.11) Inhibitors," *J. Med. Chem.* 37:498-511, American Chemical Society (1994).

De Waziers, I., et al., "Cytochrome P 450 Isoenzymes, Epoxide Hydrolase and Glutathione Transferases in Rat and Human Hepatic and Extrahepatic Tissues," *The Journal of Pharmacology and Experimental Therapeutics*, vol. 253, No. 1, 387-394, The American Society for Pharmacology and Experimental Therapeutics (1990).

Deeks, S.G., et al., "The Safety and Efficacy of Adefovir Dipivoxil, a Novel Anti—Human Immunodeficiency Virus (HIV) Therapy, in HIV-Infected Adults: A Randomized, Double-Blind, Placebo-Controlled Trial," *The Journal of Infectious Diseases*, vol. 176, 1517-23, The University of Chicago (1997).

Desos, P., et al., "Structure-Activity Relationships in a Series of 2(1*H*)-Quinolones Bearing Different Acidic Function in the 3-Position: 6,7-Dichloro-2(1*H*)-oxoquinoline-3-phosphonic Acid, a New Potent and Selective AMPA/Kainate Antagonists with Neuroprotective Properties," *J. Med. Chem.* 39:197-206, American Chemical Society (1996).

Dickson, J.K., et al., "Orally Active Squalene Synthase Inhibitors: Bis((acyloxy)alkyl) Prodrugs of the α-Phosphonosulfonic Acid Moiety," *J. Med. Chem.* 39:661-664, American Chemical Society (1996).

Dyatkina, Natalja, et al., "Synthesis of the Four Possible Stereoisomeric 5'-Nor Carbocyclic Nucleosides from One Common Enantiomerically Pure Starting Material," *Tetrahedron Letters* 35/13:1961-1994, Elsevier Science Ltd. (1994).

Edmundson, R.S., et al., "Cyclic Organophosphorous Compounds. Part 23. Configurational Assignments in the 4-Phenyl-1,3,2λ-dioxaphosphorinane Series. *X*-Ray Molecular Structure of cis-2-Benzylamino-4-phenyl-1,3-2-dioxaphosphorinane 2-Oxide," *J. Chem. Research (S)*, 122-123, Science Reviews Ltd. (1989).

Enriquez, P., et al., "Conjugation of Adenine Arabinoside 5'-Monophosphate to Arabinogalactan: Synthesis, Characterization, and Antiviral Activity," *Bioconjugate Chem.* 6:195-202, American Chemical Society (1995).

Erion, M., et al., "Design, Synthesis, and Characterization of a Series of Cytochrome $P_{450}$ 3A-Activated Prodrugs (HepDirect Prodrugs) Useful for Targeting Phosph(on)ate-Based Drugs to the Liver," *J. Am. Chem. Soc.* 126:5154-5163, American Chemical Society (Apr. 2004).

Erion, M., et al., "HepDirect™ Prodrugs: A Novel Strategy for Targeting Drugs to the Liver," *Hepatology* 36:301A, AASLD Abstract No. 551, John Wiley & Sons, Inc. (Oct. 2002).

Erion, M., et al., "HepDirect Prodrugs for Targeting Nucleotide-Based Antiviral Drugs to the Liver," *Curr. Opin. Invest. Drugs* 7(2):109-117, The Thomson Corporation (2006).

Erion, M., et al., "Liver-Targeted Drug Delivery Using HepDirect Prodrugs" *J. Pharmacol. Exper. Ther.* 312:554-560, American Society for Pharmacology and Experimental Therapeutics (Feb. 2005).

Erion, M., "Liver-Targeted Nucleoside Prodrugs," presented at the *Gordon Research Conference: Purines, Pyrimidines and Related Substances*, Newport, RI (Jun.-Jul. 2003).

Evans, D.A., et al., "Double Stereodifferentiating Aldol Reactions. The Documentation of 'Partially Matched' Aldol Bond Constructions in the Assemblage of Polyproprionate Systems," *J. Am. Chem. Soc.*, vol. 117, 9073-9074, American Chemical Society (1995).

Farquhar, D., et al., "Biologically-Cleavable Phosphate Protective Groups: 4-Acyloxy-1,3,2-Dioxaphosphorinanes as Neutral Latent Precursors of Dianionic Phosphates," *Tetrahedron Lett.* 36:655-658, Elsevier Science Ltd. (1995).

Farquhar, D. and Smith, R., "Synthesis and Biological Evaluation of 9-[5'-(2-Oxo-1,3,2-oxazaphosphorinan-2-yl)- β -D-arabinosyl]adenine and 9-[5-(2-Oxo-1,3,2-dioxazaphosphorinan-2-yl)- β -D-arabinosyl]adenine: Potential Neutral Precursors of 9-[β -D-Arabinofuranosyl]adenine 5'-Monophosphate," *J. Med. Chem.* 28:1358-1361, American Chemical Society (1985).

Farquhar, D., et al., "5'-4-(Pivaloyloxy)-1,3,2-dioxaphosphorinan-2-yl]-2'-deoxy-5-fluorouridine: A Membrane-Permeating Prodrug of 5-Fluoro-2'-deoxyuridylic Acid (FdUMP)," *J. Med. Chem.* 38:488-495, American Chemical Society (1995).

Farquhar, D., et al., "Synthesis and Antitumor Evaluation of Bis[(pivaloyloxy) methyl] 2'- Deoxy-5-fluorouridine 5'-Monophosphate (FdUMP): A Strategy to Introduce Nucleotides into Cells," *J. Med. Chem.* 37:3902-3909, American Chemical Society (1994).

Farquhar, D., et al., "Synthesis and Biological Evaluation of Neutral Derivatives of 5-Fluoro-2'-deoxyuridine 5'-Phosphate," *J. Med. Chem.* 26:1153-1158, American Chemical Society (1983).

Fiume, L., et al., "Inhibition of Hepatitis B Virus Replication by Vidarabine Monophosphate Conjugated with Lactosaminated Serum Albumin," *The Lancet* 2:13-15, The Lancet Publishing Group (1988).

Freed, J.J., et al., "Evidence for Acyloxymethyl Esters of Pyrimidine, 5'-Deoxyribonucleotides as Extracellular Sources of Active 5'-Deoxyribonucleotides in Cultured Cells," *Biochem. Pharm.* 38:3193-3198, Elsevier Inc. (1989).

Friis, G.J. and Bundgaard, H., "Prodrugs of phosphates and phosphonates: Novel lipophilic α-acyloxyalkyl ester derivatives of phosphate- or phosphonate containing drugs masking the negative charges of these groups," *Euro. J. Pharm. Sci.* 4:49-59, Elsevier Science B.V. (1996).

Furegati, S., et al., "Sterochemistry of the Inhibition of σ-Chymotrypsin with Optically Active cis-Decaline-Type Organosphosphates: $^{31}$P-NMR Studies," Helvetica Chimica Acta 81:1127-1138, Wiley-VCH Verlag GmbH & Co. KGaA (1998).

Gao, Y. et al. "Asymmetric Synthesis of Both Enantiomers of Tomoxetine and Fluoxetine. Selective Reduction of 2,3-Epoxycinnamyl Alcohol with Red-A1" J. Org. Chem. 53, 4081-4084 (1988).

Ghosh, A.K., et al., "Highly Diastereoselective anti-Aldol Reactions Utilizing the Titanium Enolate of cis-2-Arylsulfonamido-1-acenaphthenyl Propionate," Organic Letters, vol. 5, No. 7, 1063-1066, American Chemical Society (2003).

Ghosh, A.K., et al., "Synthesis of Enantiomerically Pure Anti-Aldols: A Highly Stereoselective Ester-Derived Titanium Enolate Aldol Reaction," J. Am. Chem. Soc., vol. 118, 2527-2528, American Chemical Society (1996).

Gilead Press Release, "Gilead Achieves Primary Endpoint in Phase III Study of Adefovir Dipivoxil for Chronic Hepatitis B Virus Infection," (2001).

Groen, A.K., et al., "Intracellular Compartmentation and Control of Alanine Metabolism in Rat Liver Parenchymal Cells," Eur. J. Biochem. 122:87-93, The Federation of European Biochemical Societies and Blackwell Publishing (1982).

Guida, W.C., et al., "Structure-Based Design of Inhibitors of Purine Nucleoside Phosphorylase. 4. A Study of Phosphate Mimics," J. Med. Chem. 37:1109-1114, American Chemical Society (1994).

Harada, T., et al., "Resolution of 1,3-Alkanediols Via Chiral Spiroketals Derived from l-Menthone," Tetrahedron Letters, vol. 28, No. 41, 4843-4846, Pergamon Journals Ltd. (1987).

Hatse, S., "Mechanistic Study on the Cytostatic and Tumor Cell Differentiation-inducing properties of 9-(2-Phosphonylmethoxyethyl)adenine (PMEA, adefovir)-collected Publications," Verh K Acad Geneeskd Belg, vol. 62(5):373-84 (2000).

He, K., et al., "Inactivation of Cytochrome P450 3A4 by Bergamottin, a Component of Grapefruit Juice," Chem. Res. Toxicol. 11:252-259, American Chemical Society (1998).

Hillers, S., et al., "Analogs of pyrimidinemono-and polynucleotides. VI. Phosphates of 1-(1,4-dihydroxy-2-pentyl)thymine and 1-(1,3-dihydroxy-2-propyl) uracil," Chemical Abstracts 89(17), Chemical Abstracts Service (1978).

Hirayama, N., et al., "Structure and conformation of a novel inhibitor of angiotensin I converting enzyme—a tripeptide containing phosphonic acid," Int. J. Pept. Protein Res. 38:20-24, Blackwell Publishing (1991).

Hirano, S., et al., "Practical Perparation of N-(1-Alkynyl)sulfonamides and Their Remote Diastereoselective Addition to Aldehydes via Titanation," Organic Letters, vol. 6, No. 5, 727-729, American Chemical Society (2004).

Holy, A., et al., "Acyclic Nucletotide Analogues: Synthesis, Antiviral Activity and Inhibitory Effects on some Cellular and Virus-Encoded Enzymes in Vitro," Antiviral Research, vol. 13, Issue 6, 295-311, Elsevier Science B.V. (1990).

Hong, Z. and Lin, C.-C., "Clinical Update of Remofovir (Hepavir B): a Liver-targeting Prodrug of PMEA for the Treatment of Hepatitis B," Presented at the SRI-Antiviral Drug Discovery & Development Summit, Mar. 30, 2004.

Hong, Z., "Hepavir B: a Safer and Liver-Targeting Prodrug of PMEA," Presented at the SRI-Antiviral Drug Discovery & Development Summit, Ribopharm Inc., Mar. 27, 2003.

Hunston, R., et al., "Synthesis and Biological Properties of Some Cyclic Phosphotriesters Derived from 2'-Deoxy-5-fluorouridine," J. Med. Chem. 27:440-444, American Chemical Society (1984).

Inanaga, J. et al., "A Rapid Esterification by Means of Mixed Anhydride and Its Application to Large-ring Lactonization" Bulletin of the Chemical Society of Japan, vol. 52(7): 1989-1993 (1979).

Itoh, Y., "Direct Generation of Ti-Enolate of α-CF$_3$ Ketone: Theoretical Study and High-Yielding and Diastereoselective Aldol Reaction," J. Am. Chem. Soc., vol. 126, 13174-13175, American Chemical Society (2004).

Jones, S., et al., "An Improved Method for Lewis Acid Catalyzed Phosphoryl Transfer with Ti(t-BuO)$_4$," J. Org. Chem, vol. 68, 5211-5216, American Chemical Society (2003).

Jones, S., et al., "Catalytic Phosphorylation using a Bifunctional Imidazole Derived Nucleophilic Catalyst," Chem. Commun., 3832-3834, The Royal Society of Chemistry (2005).

Jones, S., et al., "N-Phosphoryl Oxazolidinones as Effective Phosphorylating Agents," Tetrahedron Letters, vol. 45, 1585-1588, Elsevier Ltd. (2004).

Jones, S., et al., "Phosphorylation of Alcohols with N-Phosphoryl Oxazolidinones Employing Copper(II) Triflate Catalysis," Organic Letters, vol. 7, No. 15, 3271-3274, American Chemical Society (2005).

Keenan, R., et al., "Pathology Reevaluation of the Kociba et al. (1978) Bioassay of 2,3,7,8-TCDD: Implications for Risk Assessment," J. Tox. Envir. Health 34:279-296, Hemisphere Publishing Corporation (1991).

Kelley, J.L., et al., "[[(Guaninylalkyl)phosphinico]methyl]phosphonic Acids. Multisubstrate Analogue Inhibitors of Human Erythrocyte Purine Nucleoside Phosphorylase," J. Med. Chem. 38:1005-1014, American Chemical Society (1995).

Khamnei, S. et al. "Neighboring Group Catalysis in the Design of Nucleotide Prodrugs" J. Med. Chem. 39, 4109-4115 (1996).

Khorana, H.G., et al., "Cyclic Phosphates. III. Some General Observations on the Formation of Properties of Five-,Six- and Seven-membered Cyclic Phosphate Esters," J. Am. Chem. Soc. 79:430-436, American Chemical Society (1957).

Kobayashi, T., et al., "Acylation of Active Methylene Compounds via Palladium Complex-Catalyzed Carbonylative Cross-Coupling of Organic Halides," Tetrahedron Letters, vol. 27, No. 39, 4745-4748, Pergamon Journals Ltd. (1986).

Koch, G., et al., "Diastereoselective Titanium Enolate Aldol Reaction for the Total Synthesis of Epothilones," Organic Letters, vol. 4, No. 22, 3811-3814, American Chemical Society (2002).

Koep, S., et al., "Asymmetric Synthesis of Unsaturated, Fused Bicyclic Proline Analogues through Amino Alkylation of Cyclic Bis(allylsulfoximine)titanium Complexes and Migratory Cyclization of δ-Amino Alkenyl Aminosulfoxonium Salts," J. Am. Chem. Soc., vol. 125, 13243-13251, American Chemical Society (2003).

Korba, B.A., et al., "Liver-Targeted Antiviral Nucleosides: Enhanced Antiviral Activity of Phosphatidyl-Dideoxyguanosine in Woodchuck Hepatitis Virus Infection In Vivo," Hepatology 23:958-963, John Wiley & Sons, Inc. (1996).

Kryuchkov, A.A., et al., "Influence of Solvent on the Strength of Cyclic Oxygen-Containing Phosphorus Acids," Bull. Acad. Sci. USSR, A translation of Izvestiya Akademii Nauk SSSR, Ser. Khim. 36:1145-1148, Consultants Bureau (1987).

Lau, D., et al., "Safety, Tolerablity, Pharmacokinetics and Pharmacodynamics of Remofovir in Chronic HBV Patients in USA and Canada Following Daily Dosing for 28 Days," Presented at the 40$^{th}$ Annual Meeting of EASL, Paris, France, J. Hepatology 42(Suppl. 2):32, Abstract No. 74, Elsevier Ireland Ltd. (Apr. 2005).

Lefebvre, I., et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," J. Med. Chem. 38:3941-3950, American Chemical Society (1995).

Li, Yuan et al. "Synthesis of D-arabinofuranosides Using Propane-1,3-diyl Phosphate as the Anomeric Leaving Group" Tetrahedron Letters 42: 6615-6618 Elsevier Sciences Ltd. (2001).

Lin, C.-C., et al., "Development of Hepavir B, A Prodrug of PMEA with Excellent Liver-Targeting Properties," Abstacts of the 39$^{th}$ Annual Meeting of the EASL, Berlin, Germany, J. Hepatology 40:Abstract No. 374, Elsevier Ireland Ltd. (Apr. 2004).

Lin, C.-C., et al., "Pradefovir is a Substrate, but Neither an Inhibitor nor an Inducer for Cytochrome P450," AASLD Abstracts, Hepatology 514A:Abstract No. 811, John Wiley & Sons, Inc. (Oct. 2005).

Lin, C.-C., et al., "Remofovir mesylate: a prodrug of PMEA with improved liver-targeting and safety in rats and monkeys," Antiviral Chem. Chemother. 15:307-316, International Medical Press (2004).

Lin, C.-C., et al., "Safety, Tolerance, Pharmacokinetics and Pharmacodynamics of Remofovir, A Liver-Targeting Prodrug of PMEA in HBV Patients Following Daily Dosing for 28 Days," AASLD Abstracts, Hepatology 40:658A, Abstract No. 1141, John Wiley & Sons, Inc. (Oct. 2004).

Lok, A.S.F., et al., "Neurotoxicity associated with adenine arabinoside monophosphate in the treatment of chronic hepatitis B virus infection," *J. Antimicrob. Chemotherap.* 14:93-99, Oxford University Press (1984).

Lovely, C.J., et al., "Synthesis of Bridged Medium-Sized Rings through the Intramolecular Pauson-Khand Reaction," *Organic Letters*, vol. 3, No. 16, 2607-2610, American Chemical Society (2001).

Lu, X. and Zhu, J., "Palladium-Catalyzed Reaction of Aryl Polyfluoroalkanesulfonates with O,O-Dialkyl Phosphonates," *Synthesis* (8):726-727, Georg Thieme Verlag (1987).

Ludeman, S.M., et al., "Synthesis and Antitumor Activity of Cyclophosphamide Analogues. 4. Preparation, Kinetic Studies, and Anticancer Screening of "Phenylketophosphamide" and Similar Compounds Related to the Cyclophosphamide Metabolite Aldophosphamide," *J. Med. Chem.* 29:716-727, American Chemical Society (1986).

Lundgren, S., et al., "Dual Lewis Acid—Lewis Base Activation in Enantioselective Cyanation of Aldehydes Using Acetyl Cyanide and Cyanoformate as Cyanide Sources," *J. Am. Chem. Soc.*, vol. 127, 11592-11593, American Chemical Society (2005).

Maragni, P., et al., "Preparation of the Key Intermediate in the Synthesis of GV143253A: The Anti-MRSA/E Injectable Trinem," *Organic Process Research & Development*, vol. 6, No. 5, 597-605, American Chemical Society (2002).

Martin, John C. et al. "Synthesis and Antiviral Activity of Various Esters of 9-[(1,3-Dihydroxyl-2-propoxy)methyl]guanine"*J. Pharmaceutical Sciences* 76/2: 180-184 American Pharmaceutical Association (1987).

Matsumura, Y., et al., "Dependence of the Reactivities of Titanium Enolates on How They are Generated: Diastereoselective Coupling of Phenylacetic Acid Esters Using Titanium Tetrachloride," *J. Org. Chem.*, vol. 61, 2809-2912, American Chemical Society (1996).

McGuigan, C., et al., "Intracellular Delivery of Bioactive AZT Nucleotides by Aryl Phosphate Derivatives of AZT," *J. Med. Chem.* 36:1048-1052, American Chemical Society (1993).

McGuigan, C., et al., "Kinase Bypass: A New Strategy for Anti-HIV Drug Design," *Bioorg. Med. Chem. Lett.* 3:1207-1210, Pergamon Press Ltd. (1993).

Meier, C., et al., "Cyclic Saligenyl Phosphotriesters of 2',3'-Dideoxy-2',3'-didehydrothymidine (d4T)—A New Pro-Nucleotide Approach—" *Bioorg. Med. Chem. Lett.* 7:99-104, Elsevier Science Ltd. (1997).

Meijer, D.K.F., et al., "Covalent and Noncovalent Protein Binding of Drugs: Implications for Hepatic Clearance, Storage, and Cell-Specific Drug Delivery," *Pharm. Res.* 6:105-118, Plenum Publishing Corporation (1989).

Melvin, L.S., "An Efficient Synthesis of 2-Hydroxyphenylphosphonates," *Tetrahedron Lett.* 22:3375-3376, Pergamon Press Ltd. (1981).

Meyer, R., et al., "2'-O-Acyl-6-thioinosine Cyclic 3',5'-Phosphates as Prodrugs of Thioinosinic Acid," *J. Med. Chem.* 22:811-815, American Chemical Society (1979).

Mitchell, A., et al., "Bioreversible Protection for the Phospho Group: Bioactivation of the Di(4-acyloxybenzyl) and Mono(4-acyloxybenzyl) Phosphoesters of Methylphosphonate and Phosphonacetate," *J. Chem. Soc. Perkins Trans. 1*, 2345-2353, Royal Society of Chemistry (1992).

Mitsunobu, O. "The Use of Diethyl Azodicarboxylate and Triphenylphosphine in Synthesis and Transformation of Natural Products" *Synthesis* 1-28 (1981).

Moore, M., et al., "Comparison of mutagenicity results for nine compounds evaluated at the *hgprt* locus in the standard and suspension CHO assays," *Mutagenesis* 6:77-85, Oxford University Press (1991).

Moriarty, R. M., et al., "Diphenyl Methylphosphonate as a Phosphonylation Reagent with High Diastereoselectivity at Phosphorus," *Tetrahedron Letters*, vol. 38, No. 15, 2597-2600, Elsevier Science Ltd. (1997).

Mosbo, J.A. and Verkade, J.G., "Dipole Moment, Nuclear Magnetic Resonance, and Infrared Studies of Phosphorus Configurations and Equalibria in 2-R-2-Oxo-1,3,2-dioxaphosphorinames," *J. Org. Chem.* 42:1549-1555, American Chemical Society (1977).

Mukaiyama, T., "Ch. 3: The Directed Aldol Reaction," *Organic Reactions* 28:203-331 (1982).

Mulato, A.S., et al., "Nonsteroidal Anti-Inflammatory Drugs Efficiently Reduce the Transport and Cytotoxicity of Adefovir Mediated by the Human Renal Organic Anion Transporter 1," *J. Pharm. Exp. Ther.* 295:10-15, American Society for Pharmacology and Experimental Therapeutics (2001).

Murono, S., et al., "Prevention and Inhibition of Nasopharyngeal Carcinoma Growth by Antiviral Phosphonated Nucleoside Analogs," *Cancer Research*, vol. 61, 7875-7877 (2001).

Murray, G., et al., "Cytochrome P450 CYP3A in human renal cell cancer," *Brit. J. Cancer* 79:1836-1842, Nature Publishing Group (1999).

Murray, G., et al., "Cytochrome P450 Expression Is a Common Molecular Event in Soft Tissue Sarcomas," *J. Pathology* 171:49-52, John Wiley & Sons, Ltd. (1993).

Naesens, L. et al., "HPMPC (cidofovir), PMEA (adefovir) and Related Acyclic Nucleoside Phosphonate Analogues: A Review of their Pharmacology and Clinical Potential in the Treatment of Viral Infections" *Antiviral Chemistry and Chemotherapy* 8(1): 1-23 International Medical Press Ltd. (1997).

Naesens, L., et al., "Therapeutic Potential of HPMPC (Cidofovir), PMEA (Adefovir) and Related Acyclic Nucleoside Phosphonate Analogues as Broad-Spectrum Antiviral Agents," *Nucleosides & Nucleotides*, 16(7-9), 983-992, Marcel Dekker, Inc. (1997).

Nakayama, K. and Thompson, W.J., "A Highly Enantioselective Synthesis of Phosphate Triesters," *J. Am. Chem. Soc.* 112:6936-6942, American Chemical Society (1990).

Neidlein, R., et al., "Mild Preparation of 1-Benzyloxyiminoalkylphosphonic Dichlorides: Application to the Synthesis of Cyclic Phosphonic Deisters and Cyclic Monoester Amides," *Heterocycles* 35:1185-1203, Elsevier Science (1993).

Nifantyev, E.E., et al., "Synthesis and Structure of Some Stable Phospholane-Phospholanes," *Phosphorus, Sulfur and Silicon and Related Elements* 113:1-13, Taylor & Francis (1996).

Noble, S. and Goa, K.L., "Adefovir Dipivoxil," *Drugs* 58:479-487, Adis International Ltd. (1999).

Ogg, M., et al., "A reporter gene assay to assess the molecular mechanisms of xenobiotic-dependent induction of the human CYP3A4 gene in vitro," *Xenobiotica* 29:269-279, Taylor & Francis Ltd. (1999).

Ohashi, K. et al. "Synthesis of Phosphonosphingoglycolipid Found in Marine Snail *Turbo Cornutus*" *Tetrahedron Lett.* 29(10), 1189-1192 (1988).

Oliyai, R., et al., "Kinetic Studies of the Degradation of Oxycarbonyloxymethyl Prodrug of Adefovir and Tenofovir in Solution," *Nucleosides, Nucleotides & Nucleic Acids*, vol. 20, (4-7), 1295-1298, Marcel Dekker, Inc. (2001).

Patois, C., et al., "Easy Preparation of Alkylphosphonyl Dichlorides," *Bull Soc. Chim. Fr.*, vol. 130, 485-487, Elsevier (1993).

Periasamy, M., "New Synthetic Methods Using the $TiCl_4$-$NR_3$ Regeant System," *ARKIVOC*, (VII), 151-166, ARKAT (2002).

Petrakis, K. and Nagabhushan, T.L., "Palladium-Catalyzed Substitutions of Triflates Derived from Tyrosine-Containing Peptides and Simpler Hydroxyarenes Forming 4-(Diethoxyphosphinyl)phenylalanines and Diethyl Arylphosphonates," *J. Am. Chem. Soc.* 109:2831-2833, American Chemical Society (1987).

Phillion, D.P., "Synthesis and Reactivity of Diethyl Phosphonomethyltriflate," *Tetrahedron Letters*, vol. 27, No. 13, 1477-1480, Pergamon Press Ltd. (1986).

Pitcher, H.R., "Built-in Bypass," *Nature* 429:39, Nature Publishing Group (May 2004).

Predvoditelev, D.A., et al., "Glycero-2-Hydroxymethylene Phosphates," *J. Org. Chem. USSR, A Translation of Zhur. Org. Khim.* 13:1489-1492, Plenum Publishing Corporation (1977).

Predvoditelev, D.A., et al., "Synthesis of Lipids and Their Models on the Basis of Glycerol Alkylene Phosphites. V. Cyclic Phosphatidylglycerol and Phosphatidylhydroxyhomocholine," *J. Org. Chem. USSR, A Translation of Zhur. Org. Khim.* 17:1156-1165, Plenum Publishing Corporation (1981).

Ramachandran, P. V., et al., "Efficient General Synthesis of 1,2- and 1,3-Diols in High Enantiomeric Excess via the Intramolecular Asymmetric Reduction of the Corresponding Ketoalkyl Diisopinocampheylborinate Intermediates," *Tetrahedron Letters*, vol. 38, No. 5, 761-764, Elsevier Science Ltd. (1997).

Reddy, L. R., et al., "Asymmetric Synthesis of *anti*-Homopropargylic Alcohols from Aldehydes and Chiral Sulfonimidoyl Substituted Bis(allyl)titanium Complexes through Generation and Elimination of Novel Chiral Alkylidenecarbene (Dimethylamino)sulfoxonium Ylides," *J. Am. Chem. Soc.*, vol. 124, 10427-10434, American Chemical Society (2002).

Reddy, K.R., et al., "Stereoselective synthesis of nucleoside monophosphate HepDirect™ prodrugs," *Tetrahedron Lett.* 46:4321-4324, Elsevier Ltd. (2005).

Reddy, M.R., et al., "Development of a Quantum Mechanics-Based Free-Energy Perturbation Method: Use in the Calculation of Relative Solvation Free Energies," *J. Am. Chem. Soc.* 126:6224-6225, American Chemical Society (published online Apr. 2004).

Redmore, D., "Phosphorus Derivatives of Nitrogen Heterocycles. 2. Pyridinophosphonic Acid Derivatives," *J. Org. Chem.* 35:4114-4117, American Chemical Society (1970).

Russell, J.W., et al., "Determination of 9-[(2-phosphonylmethoxyl)ethyl]ethyl]adenine in rat urine by high-performance liquid chromatography with fluorescence detection," *J. Chromatogr.* 572:321-326, Elsevier Science Publishers (1991).

Sagar, R., et al., "A Substrate Controlled, Very Highly Diastereoselective Morita-Baylis-Hillman Reaction: a Remote Activation of the Diastereofacial selectivity in the Synthesis of C-3-branched Deoxysugars," *Tetrahedron*, vol. 60, 11399-11406, Elsevier Ltd. (2004).

Sakamoto, T., et al., "The Palladium-Catalyzed Arylation of 4*H*-1,3-Dioxin," *Tetrahedron Letters*, vol. 33, No. 45, 6845-6848, Pergamon Press Ltd. (1992).

Santra, S., et al., Diastereoselective, Titanium-Mediated Cyclization of ω-Vinyl Tethered Imides, *Organic Letters*, vol. 7, No. 26, 5901-5904, American Chemical Society (2005).

Sato, K., et al., "Highly Diastereoselective Reductive Coupling of 2-Bromo-2,3,3,3-tetrafluoropropanamide with Aldehydes Promoted by Triphenylphosphine—Titanium(IV) Isopropoxide. An Efficient Route to the Synthesis of *erythro*-α-Fluoro-α-(trifluoromethyl)-β-hydroxy Amides," *J. Org. Chem.*, vol. 69, 5041-5047, American Chemical Society (2004).

Schlachter, S.T., et al., "Anti-Inflammatory/Antiarthritic Ketonic Bisphosphonic Acid Esters," *Bioorg. Med. Chem. Lett.* 8:1093-1096, Elsevier Science Ltd. (1998).

Schultz, C. "Prodrugs of Biologically Active Phosphate Esters" *Bioorganic & Medicinal Chemistry* 11:885-898, Elsevier Science Ltd. (Mar. 2003).

Schultze, L.M. et al., "Practical Synthesis of the anti-HIV Drug, PMPA" *Tetrahedron Lett.* 39:1853-1856, Elsevier Science Ltd. (1998).

Serafinowska, H. T., et al., "Synthesis and in Vivo Evaluation of Prodrugs of 9-[2-(Phosphonomethoxy)ethoxy]adenine," *J. Med. Chem.*, vol. 38, 1372-1379, American Chemical Society (1995).

Shaw, J.-P., et al., "Pharmacokinetics and Metabolism of Selected Prodrugs of PMEA in Rats," *Drug Metabolism and Disposition*, vol. 25, No. 3: 362-366, The American Society for Pharmacology and Experimental Therapeutics (1997).

Shaw, J.-P. and Cundy, K.C., "Biological Screens of PMEA Prodrugs," *Pharm. Res.* 10:S-294, Kluwer Academic Publishers B.V., Abstract No. PDD 7480 (1993).

Shih, Y.-E., et al., "Preparation and Structures of 2-Dimethylamino-4-phenyl-1,3,2-dioxaphosphorinane-2-oxides," *Bull. Inst. Chem. Acad. Sin.* 41:9-16, Academia Sinica, Nankang, Taipei, Taiwan (1994).

Starrett, J. E., Jr., et al., "Synthesis, Oral Bioavailability Determination, and in Vitro Evaluation of Prodrugs of the Antiviral Agent 9-[2-(Phosphonomethoxy)ethyl]adenine (PMEA)," *J. Med. Chem.*, vol. 37, 1857-1864, American Chemical Society (1994).

Still, W.C., et al., "Direct Synthesis of Z-Unsaturated Esters. A Useful Modification of the Horner-Emmons Olefination," *Tetrahedron Letters*, vol. 24, No. 41: 4405-4408 Pergamon Press Ltd. (1983).

Stowell, M.H.B., et al., "The Mild Preparation of Synthetically Useful Phosphonic Dichlorides: Application to the Synthesis of Cyclic Phosphonic Diesters and Diamedes," *Tetrahedron Letters*, vol. 31, No. 23, 3261-3262, Pergamon Press plc (1990).

Sullivan-Bolyai, J., et al., "Safety, Tolerability, Antiviral Activity, and Pharmacokinetics of Pradefovir Mesylate in Patients with Chronic Hepatitis B Virus Infection: 24-Week Interim Analysis of a Phase 2 Study," AASLD Program, *Hepatology* 78A: Abstract No. LB 07, John Wiley & Sons, Inc. (Oct. 2005).

Tawfik, D.S., et al., "1,8-Diazabicyclo[5.4.0]undecene Mediated Transesterification of *p*-Nitrophenyl Phosphonates: A Novel Route to Phosphono Esters," *Synthesis* 968-972 (1993).

Tang, T. P., et al., "Asymmetric Synthesis of β-Amino Acid Derivatives Incorporating a Broad Range of Substitution Patterns by Enolate Additions to *tert*-Butanesulfinyl Imines," *J. Org. Chem.*, vol. 67, 7819-7832, American Chemical Society (2002).

Ten Hoeve, W. and Wynberg, H. "The Design of Resolving Agents. Chiral Cyclic Phosphoric Acids" *J. Org. Chem.* 50: 4508-4514. American Chemical Society (1985).

Thomson, W., et al., "Synthesis, Bioactivation and Anti-HIV Activity of the Bis(4-acyloxybenzyl) and Mono(4-acyloxybenzyl) Esters of the 5'-monophosphate of AZT," *J. Chem. Soc. Perk. Trans. 1*, 1239-1245, Royal Society of Chemistry (1993).

Turner, J. "A General Approach to the Synthesis of 1,6-,1,7-, and 1,8-Naphthyridines" *J. Org. Chem.* 55(15), 4744-4750 (1990).

Turner, J. A., et al., "Acylation of Ester Enolates by *N*-Methoxy,-*N*-methylamides: An Effective Synthesis of β-Keto Esters," *J. Org. Chem.*, vol. 54, 4229-4231, American Chemical Society (1989).

Van Poelje, P., et al., "MB6866 (Hepavir B), A HepDirect™ Prodrug of Adefovir: Mechanism of Activation and Liver Targeting," AASLD Abstracts, *Hepatology* 706A: Abstract No. 1143, John Wiley & Sons, Inc. (Oct. 2003).

Venook, A., "Treatment of Hepatocellular Carcinoma: Too Many Options?," *J. Clin. Oncol.* 12:1323-1334, American Society of Clinical Oncology (1994).

Vo-Quang, Y., et al., "(1-Amino-2-propenyl)phosphonic Acid, an Inhibitor of Alanine Racemase and D-Alanine:D-Alanine Ligase," *J. Med. Chem.* 29:579-581, American Chemical Society (1986).

Wacher, V.J., et al., "Active Secretion and Enterocytic Drug Metabolism Barriers to Drug Absorption," *Advanced Drug Delivery Reviews*, vol. 46, 89-102, Elsevier Science B. V. (2001).

Wagner, A., et al., "Direct Conversion of Tetrahydropyranylated Alcohols to the Corresponding Bromides," *Tetra. Lett.* 30:557-558, Pergamon Press plc (1989).

Wallace, E.M., et al., "Design and Synthesis of Potent, Selective Inhibitors of Endothelin-Converting Enzyme," *J. Med. Chem.* 41:1513-1523, American Chemical Society(1998).

Walsh, E., et al., "Phenoxymethylphosphonic Acids and Phosphonic Acid Ion-exchange Resins," *Phenoxymethylphosphonic Acid Ion-Exchange Resins* 78:4455-4458, American Chemical Society (1956).

Watkins, P., "Noninvasive tests of CYP3A enzymes," *Pharmacogenetics* 4:171-184, Lippincott Williams & Wilkins (1994).

Weber, G.F. and Waxman, D.J., "Activation of the Anti-cancer Drug Ifosphamide by Rat Liver Microsomal P450 Enzymes," *Biochem. Pharm.* 45:1685-1694, Pergamon Press Ltd. (1993).

Weibel, M., et al., "Potentiating Effect of {2-[2-[(2-Amino-1,6-Dihydro-6-Oxo-9H-Purin-9-yl)Methyl]-Phenyl] Ethenyl}-Phosphonic Acid (MDL 74,428), A Potent Inhibitor of Purine Nucleoside Phosphorylase, on the Antiretroviral Activities of 2',3'-Dideoxyinosine Combined to Ribavirin in Mice," *Biochem. Pharmacol.* 48:245-252, Elsevier Science Ltd. (1994).

Wileman, T., et al., "Receptor-mediated endocytosis," *Biochem. J.* 232:1-14, Portland Press (1985).

Yadav, V.K., et al., "Diastereoselective Aldol Reactions of Enolates Generated from Vicinally Substitued Trimethylsilylmethyl Cyclopropyl Ketones," *Organic Letters*, vol. 5, No. 23, 4281-4284, American Chemical Society (2003).

Yamamoto, J., et al., "Synthesis of Pyridine N-Oxide-SbCl$_5$ Complexes and their Intramolecular and Oxygen-Transfer Reaction," *Tetrahedron*, vol. 37, 1871-1873, Pergamon Press Ltd. (1981).

Yeori, A., et al., "Diastereoisomerically Selective Enantiomerically Pure Titanium Complexes of Salan Ligands: Synthesis, Structure, and Preliminary Activity Studies," *Inorg. Chem.*, vol. 44, 4466-4468, American Chemical Society (2005).

Yu, L. J., et al., "In vivo Modulation of Alternative Pathways of P-450-Catalyzed Cyclophosphamide Metabolism: Impact on Pharmacokinetics and Antitumor Activity," *J. Pharmacol. Exp. Ther.* 288:928-937, The American Society for Pharmacology and Experimental Therapeutics (1999).

Zon, G., "Cyclophosphamide Analogues" in *Progress in Medicinal Chemistry*, Ellis, G.P., et al., eds., Elsevier Biomedical Press, Chapter 4, pp. 205-246 (1982).

Zon, G., et al., "NMR Spectroscopic Studies of Intermediary Metabolites of Cyclophosphamide. A Comprehensive Kinetic Analysis of the Interconversion of *cis*-and *trans*-4-Hydroxycyclophosphamide with Aldophosphamide and the Concomitant Partitioning of Aldophosphamide between Irreversible Fragmentation and Reversible Conjugation Pathways," *J. Med. Chem.* 27:466-485, American Chemical Society (1984).

International Search Report for related International Application No. PCT/US05/19940, United States Patent and Trademark Office, Alexandria, Virginia, USA, mailed Oct. 6, 2005.

* cited by examiner

LEWIS ACID MEDIATED SYNTHESIS OF CYCLIC ESTERS

RELATED APPLICATIONS

This application relates and claims benefit of U.S. Provisional Application Ser. No. 60/578,467 filed on Jun. 8, 2004, all of which is incorporated by reference in its entirety.

FIELD OF INVENTION

The present invention is directed towards a process of synthesis of cyclic phosphonic acid diesters from 1,3-diols. More specifically, the invention relates to an improved process wherein diastereoselectivity is increased during coupling a 1-arylpropane-1,3-diol with an activated phosphonic acid.

BACKGROUND OF THE INVENTION

The following description of the background of the invention is provided to aid in understanding the invention, but is not admitted to be, or to describe, prior art to the invention. All publications are incorporated by reference in their entirety.

Compounds containing phosphonic acids and their salts are highly charged at physiological pH and therefore frequently exhibit poor oral bioavailability, poor cell penetration and limited tissue distribution (e.g., CNS). In addition, these acids are also commonly associated with several other properties that hinder their use as drugs, including short plasma half-life due to rapid renal clearance, as well as toxicities (e.g., renal, gastrointestinal, etc.) (e.g., Bijsterbosch et al., *Antimicrob. Agents Chemother.* 42(5): 1146-50(1998)).

Phosphonic acid ester prodrugs can be used to improve the oral bioavailability, cell penetration and tissue distribution of drugs containing a phosphonic acid moiety. The most commonly used prodrug class is the acyloxyalky ester, which was first applied to phosphate and phosphonate compounds in 1983 by Farquhar et al., *J. Pharm. Sci.* 72: 324 (1983). This strategy has proven successful in the delivery of phosphates and phosphonates into cells and in the oral absorption of phosphates, phosphonate's and phosphinic acids. For example, the bis(pivoyloxymethyl) prodrug of the antiviral phosphonate, 9-(2-phosphonylmethoxyethyl)adenine (PMEA), has been studied clinically for the treatment of CMV infection and the bis(pivaloyloxymethyl) prodrug of the squalene synthetase inhibitor, BMS188494 has been evaluated as a treatment of hypercholesterolemia and associated cardiovascular diseases. The marketed antihypertensive, fosinopril, is a phosphinic acid angiotensin converting enzyme inhibitor that requires the use of an isobutryloxyethyl group for oral absorption. A close variant of the acyloxyalkyl ester strategy is the use of alkoxycarbonyloxyalkyl groups as prodrugs. These prodrugs are reported to enhance oral bioavailability.

Other examples of suitable phosphonate prodrugs include proester classes exemplified by Krise et al. (*Adv. Drug Del. Rev.* 19: 287 (1996)); and Biller and Magnin (U.S. Pat. No. 5,157,027).

Cyclic phosphonate esters have also been shown to decrease serum lipids and treat atherosclerosis (U.S. Pat. No. 5,962,440). Other examples of phosphonate esters are exemplified by Prisbe et al. (*J. Med. Chem.* 29: 671 (1986)); and Ozoe et al. (*Bioorg. Med. Chem.* 6: 73 (1998)).

SUMMARY OF THE INVENTION

The present invention is directed towards a Lewis acid catalysis process for the synthesis of a cyclic phosphonic acid diester from a 1,3-diol and an activated phosphonic acid. In one aspect, methods are described that enable diastereoselective preparation of these products. In another aspect, the methods can also be used to prepare chiral substituted cyclic phosphonic acid (or phosphonate) diesters.

One aspect of the invention concerns a method of preparing a cyclic phosphonic acid diester via reacting a chiral 1,3-diol and an activated phosphonic acid in the presence of a Lewis acid. In a further aspect, the Lewis acid is added to the chiral 1,3-diol and the diol-Lewis acid complex is added to the activated phosphonic acid.

In an additional aspect, the ratio of cis- to trans-diastereomers formed is greater than or equal to 3:1.

Also provided are methods where the Lewis acid contains an element selected from the group consisting of titanium, tin, aluminum, zinc, boron, magnesium, samarium, bismuth, iron, mercury, copper, silver and cobalt. In an additional aspect, the Lewis acid contains an element selected from the group consisting of titanium, boron, aluminum, tin, and samarium. In a further aspect, the Lewis acid contains a group independently selected from alkoxy, alkyl, aryl, or an inorganic radical. In another aspect, the Lewis acid contains a group independently selected from alkoxy, alkyl, aryl, or an inorganic radical, where the inorganic radical is selected from the group consisting of chloride, iodide, bromide, and fluoride. In a further aspect, the Lewis acid is selected from $TiCl_4$, $BF_3$, $SnCl_4$, $SmI_2$, and $AlCl_3$. An additional aspect the Lewis acid is $TiCl_4$. In a further aspect the Lewis acid is $Ti(O-(C_1-C_4)alkyl)_4$.

Also provided are methods where the activated phosphonic acid is phosphonic acid halide, phosphonic acid anhydride, or phosphonic acid carbonate. In another aspect, the activated phosphonic acid is phosphonic acid halide. In a further aspect, the phosphonic acid halide is phosphonyl chloride.

In another aspect, the method provides for adding a base selected from tertiary alkyl amines, N-containing heterocyclic aromatic bases, and non-nucleophilic inorganic bases. In a further aspect, the base is triethylamine, tri(n-butyl)amine, pyridine, quinoline or diisopropylethylamine.

In one aspect, the temperature for the reaction is −78° C. and 60° C. In another aspect, the temperature is between −20° C. and 50° C. In a further aspect, the temperature is between 15° C. and 42° C.

In one aspect, the reaction is carried out by adding 0.01 to 5 equivalents of said Lewis acid to 1.0 equivalent of said chiral 1,3-diol. In a further aspect, 0.5 to 2.0 equivalents of said Lewis acid is added.

One aspect of the invention concerns the method for the preparation of compounds of Formula I:

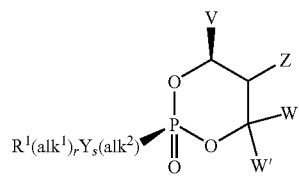

Formula I wherein:

V is selected from group consisting of phenyl, allyl, alkynyl, and monocyclic heteroaryl, all optionally substituted with 1-4 substituents;

$R^1$ is selected from the group consisting of hydrogen, optionally substituted aryl, optionally substituted heteroaryl, or $R^1$ is a group of the formula $Ar^1$-G-$Ar^2$, wherein $Ar^1$ and $Ar^2$ are aryl groups optionally substituted by lower alkyl, lower alkoxy, halogen, hydroxy, cyano, and amino, and G is —O—, —S—, —S(=O)—, —S(=O)$_2$—, —CH$_2$—, —CF$_2$—, —CHF—, —C(O)—, —CH(OH)—, —NH—, and —N($C_1$-$C_4$ alkyl)-;

$alk^1$ and $alk^2$ are the same or different and are each optionally-substituted lower alkylene;

Y is selected from the group consisting of —O—, —S—, —NR$^2$—, —C(O)—, —C(O)NR$^2$, and —NR$^2$C(O)—;

W and W' are independently selected from the group consisting of H, optionally substituted alkyl, optionally substituted alkenyl, optionally substituted alkynyl, optionally substituted monocyclic aryl, and optionally substituted monocyclic heteroaryl;

Z is selected from the group consisting of halogen, —CN, —COR$^3$, —CONR$^4{}_2$, —CO$_2$R$^3$, —CHR$^2$OC(O)R$^3$, —CHR$^2$OC(S)R$^3$, —CHR$^2$OC(O)SR$^3$, —CHR$^2$OCO$_2$R$^3$, —OR$^3$, —SR$^3$, —R$^2$, —NR$^3{}_2$, —OCOR$^3$, —OCO$_2$R$^3$, —SCOR$^3$, —SCO$_2$R$^3$, —(CH$_2$)$_p$—OR$^4$, and —(CH$_2$)$_p$—SR$^4$;

$R^2$ is hydrogen or lower alkyl;

$R^3$ is alkyl;

$R^4$ is alkyl or acyl;

p is 2 or 3;

r is 0 or 1; and s is 0 or 1.

In a further aspect, the hydroxy groups present in the formula $Ar^1$-G-$Ar^2$ may be protected.

In another aspect, said 1-(aryl)-1,3-propane diol is added to the Lewis acid and then the diol-Lewis acid complex is added to $R^1(alk^1)_rY_s(alk^2)P(O)Cl_2$ in the presence of said base.

In an additional aspect the method of preparation for compounds of Formula I provides for an increased ratio of cis to trans diastereomers. In an additional aspect, the ratio of cis- to trans- diastereomers formed is greater than or equal to 3:1.

Also provided are methods where the Lewis acid contains an element selected from the group consisting of titanium, tin, aluminum, zinc, boron, magnesium, samarium, bismuth, iron, mercury, copper, silver and cobalt. In an additional aspect, the Lewis acid contains an element selected from the group consisting of titanium, boron, aluminum, tin, and samarium. In a further aspect, the Lewis acid contains a group independently selected from alkoxy, alkyl, aryl, or an inorganic radical. In another aspect, the Lewis acid contains a group independently selected from alkoxy, alkyl, aryl, or an inorganic radical, where the inorganic radical is selected from the group consisting of chloride, iodide, bromide, and fluoride. In a further aspect, the Lewis Acid is selected from TiCl$_4$, BF$_3$, SnCl$_4$, SmI$_2$, and AlCl$_3$. In an additional aspect, the Lewis acid is TiCl$_4$. In a further aspect, the Lewis acid is Ti(O—($C_1$-$C_4$)alkyl)$_4$.

In another aspect, the method provides for adding a base selected from tertiary alkyl amines, N-containing heterocyclic aromatic bases, and non-nucleophilic inorganic bases. In a further aspect the base is triethylamine, tri(n-butyl)amine, pyridine, quinoline or diisopropylethylamine.

In one aspect, the temperature for the reaction is −78° C. and 60° C. In another aspect the temperature is between −20° C. and 50° C. In a further aspect, the temperature is between 15° C. and 42° C.

In one aspect, the reaction is carried out by adding 0.01 to 5 equivalents of said Lewis acid to 1.0 equivalent of said chiral 1,3-diol. In a further aspect, 0.5 to 2.0 equivalents of said Lewis acid is added.

Some of the compounds of Formula I have asymmetric centers where the stereochemistry is unspecified and the diastereomeric mixtures of these compounds are included as well as the individual stereoisomers when referring to a compound of Formula I generally.

In another aspect, the invention relates to a method for the preparation of compounds of Formula II:

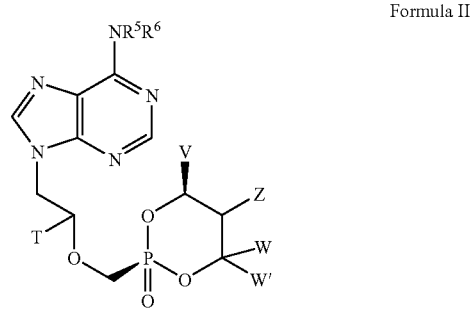

Formula II wherein,

V is selected from group consisting of aryl, and monocyclic heteroaryl, all optionally substituted with 1-4 substituents;

W and W' are independently selected from the group consisting of H, optionally substituted alkyl, optionally substituted alkenyl, optionally substituted alkynyl, optionally substituted monocyclic aryl, and optionally substituted monocyclic heteroaryl;

Z is selected from the group consisting of halogen, —CN, —COR$^3$, —CONR$^4{}_2$, —CO$_2$R$^3$, —CHR$^2$OC(O)R$^3$, —CHR$^2$OC(S)R$^3$, —CHR$^2$OC(O)SR$^3$, —CHR$^2$OCO$_2$R$^3$, —OR$^3$, —SR$^3$, —R$^2$, —NR$^3{}_2$, —OCOR$^3$, —OCO$_2$R$^3$, —SCOR$^3$, —SCO$_2$R$^3$, —(CH$_2$)$_p$—OR$^4$, and —(CH$_2$)$_p$—SR$^4$;

T is selected from the group consisting of H and lower alkyl;

$R^2$ is hydrogen or lower alkyl;

$R^3$ is alkyl;

$R^4$ is alkyl or acyl;

p is 2 or 3;

r is 0 or 1; and s is 0 or 1;

$R^5$ is a monovalent amine protecting group, and $R^6$ is hydrogen; or, $R^5$ and $R^6$ taken together are a divalent amine protecting group.

In another aspect, the method of preparing a compound of Formula II includes combining a 1-(V)-1,3-propane diol with a compound of Formula III in the presence of a Lewis acid:

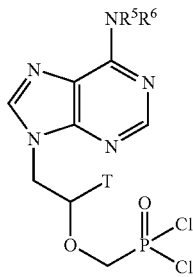

Formula III

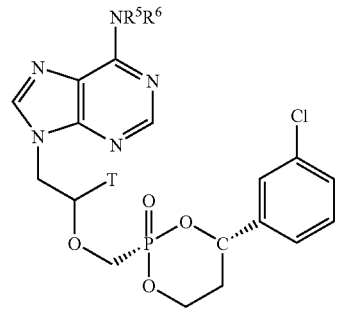

Formula IV

In an additional aspect the method of preparation for compounds of Formula II provides for an increased ratio of cis to trans diastereomers. In an additional aspect, the ratio of cis- to trans- diastereomers formed is greater than or equal to 3:1.

Also provided are methods where the Lewis acid contains an element selected from the group consisting of titanium, tin, aluminum, zinc, boron, magnesium, samarium, bismuth, iron, mercury, copper, silver and cobalt. In an additional aspect, the Lewis acid contains an element selected from the group consisting of titanium, boron, aluminum, tin, and samarium. In a further aspect, the Lewis acid contains a group independently selected from alkoxy, alkyl, aryl, or an inorganic radical. In another aspect, the Lewis acid contains a group independently selected from alkoxy, alkyl, aryl, or an inorganic radical, where the inorganic radical is selected from the group consisting of chloride, iodide, bromide, and fluoride. In a further aspect, the Lewis Acid is selected from $TiCl_4$, $BF_3$, $SnCl_4$, $SmI_2$, and $AlCl_3$. An additional aspect the Lewis acid is $TiCl_4$. In a further aspect, the Lewis acid is $Ti(O-(C_1-C_4)alkyl)_4$.

In another aspect, the method provides for adding a base selected from tertiary alkyl amines, N-containing heterocyclic aromatic bases, and non-nucleophilic inorganic bases. In a further aspect the base is triethylamine, tri(n-butyl)amine, pyridine, quinoline or diisopropylethylamine.

In one aspect, the temperature for the reaction is −78° C. and 60° C. In another aspect the temperature is between −20° C. and 50° C. In a further aspect, the temperature is between 15° C. and 42° C.

In one aspect, the reaction is carried out by adding 0.01 to 5 equivalents of said Lewis acid to 1.0 equivalent of said chiral 1,3-diol. In a further aspect, 0.5 to 2.0 equivalents of said Lewis acid is added.

Some of the compounds of Formula II have asymmetric centers where the stereochemistry is unspecified and the diastereomeric mixtures of these compounds are included as well as the individual stereoisomers when referring to a compound of Formula II generally.

The present invention provides a method for the preparation of compounds of Formula IV:

wherein $R^5$ is tert-butyloxycarbonyl, benzyloxycarbonyl, trifluoroacetyl or benzyl; and $R^6$ is hydrogen; or, $R^5$ and $R^6$ taken together are phthalimidoyl, phenylmethylidene, dimethylaminomethylidene and diethylaminomethylidene; and T is selected from the group consisting of H and lower alkyl.

An additional aspect provides a method for the preparation of compounds of Formula IV:

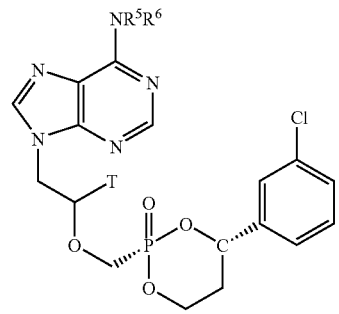

Formula IV wherein $R^5$ is tert-butyloxycarbonyl, benzyloxycarbonyl, trifluoroacetyl or benzyl; and $R^6$ is hydrogen; or, $R^5$ and $R^6$ taken together are phthalimidoyl, phenylmethylidene, dimethylaminomethylidene and diethylaminomethylidene;

T is selected from the group consisting of H and lower alkyl;

comprising:

combining (R)-1-(3-chlorophenyl)-1,3-propanediol with a compound of Formula III in the presence of a Lewis acid.

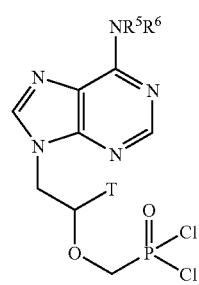

Formula III

In a further aspect of the preparation of compounds of Formula IV said (R)-1-(3-chlorophenyl)-1,3-propanediol is added to the Lewis acid and then the diol-Lewis acid complex is added to the compound of Formula III.

In an additional aspect, the method of preparation for compounds of Formula IV provides for an increased ratio of cis to trans diastereomers. In an additional aspect, the ratio of cis- to trans- diastereomers formed is greater than or equal to 3:1.

Also provided are methods where the Lewis acid contains an element selected from the group consisting of titanium, tin, aluminum, zinc, boron, magnesium, samarium, bismuth, iron, mercury, copper, silver and cobalt. In an additional aspect, the Lewis acid contains an element selected from the group consisting of titanium, boron, aluminum, tin, and samarium. A further aspect the Lewis acid contains a group independently selected from alkoxy, alkyl, aryl, or an inorganic radical. In another aspect, the Lewis acid contains a group independently selected from alkoxy, alkyl, aryl, or an inorganic radical, where the inorganic radical is selected from the group consisting of chloride, iodide, bromide, and fluoride. In a further aspect, the Lewis Acid is selected from $TiCl_4$, $BF_3$, $SnCl_4$, $SmI_2$, and $AlCl_3$. In an additional aspect, the Lewis acid is $TiCl_4$. In a further aspect, the Lewis acid is $Ti(O—(C_1-C_4)alkyl)_4$.

In another aspect, the method provides for adding a base selected from tertiary alkyl amines, N-containing heterocyclic aromatic bases, and non-nucleophilic inorganic bases. In a further aspect, the base is triethylamine, tri(n-butyl)amine, pyridine, quinoline or diisopropylethylamine.

In one aspect, the temperature for the reaction is −78° C. and 60° C. In another aspect the temperature is between −20° C. and 50° C. In a further aspect, the temperature is between 15° C. and 42° C.

In one aspect, the reaction is carried out by adding 0.01 to 5 equivalents of said Lewis acid to 1.0 equivalent of said chiral 1,3-diol. In a further aspect, 0.5 to 2.0 equivalents of said Lewis acid is added.

Some of the compounds of Formula IV have asymmetric centers where the stereochemistry is unspecified and the diastereomeric mixtures of these compounds are included as well as the individual stereoisomers when referring to a compound of Formula IV generally.

A further aspect the invention provides a method for the preparation of compounds of Formula V:

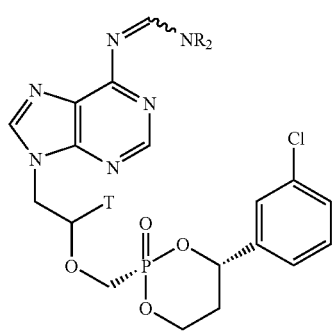

Formula V wherein R is lower alkyl and T is selected from the group consisting of H and lower alkyl. In one aspect (R)-1-(3-chlorophenyl)-1,3-propanediol is combined with a compound of Formula VI in the presence of a Lewis acid:

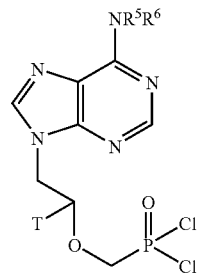

Formula VI

In a further aspect of the preparation of compounds of Formula IV said (R)-1-(3-chlorophenyl)-1,3-propanediol is added to the Lewis acid and then the diol-Lewis acid complex is added to the compound of Formula VI.

In an additional aspect the method of preparation for compounds of Formula V provides for an increased ratio of cis to trans diastereomers. In an additional aspect, the ratio of cis- to trans- diastereomers formed is greater than or equal to 3:1.

Also provided are methods where the Lewis acid contains an element selected from the group consisting of titanium, tin, aluminum, zinc, boron, magnesium, samarium, bismuth, iron, mercury, copper, silver and cobalt. In an additional aspect, the Lewis acid contains an element selected from the group consisting of titanium, boron, aluminum, tin, and samarium. In a further aspect, the Lewis acid contains a group independently selected from alkoxy, alkyl, aryl, or an inorganic radical. In another aspect, the Lewis acid contains a group independently selected from alkoxy, alkyl, aryl, or an inorganic radical, where the inorganic radical is selected from the group consisting of chloride, iodide, bromide, and fluoride. In a further aspect, the Lewis Acid is selected from $TiCl_4$, $BF_3$, $SnCl_4$, $SmI_2$, and $AlCl_3$. In an additional aspect, the Lewis acid is $TiCl_4$. In a further aspect, the Lewis acid is $Ti(O—(C_1-C_4)alkyl)_4$.

In another aspect, the method provides for adding a base selected from tertiary alkyl amines, N-containing heterocyclic aromatic bases, and non-nucleophilic inorganic bases. In a further aspect, the base is triethylamine, tri(n-butyl)amine, pyridine, quinoline or diisopropylethylamine.

In one aspect, the temperature for the reaction is −78° C. and 60° C. In another aspect, the temperature is between −20° C. and 50° C. In a further aspect the temperature is between 15° C. and 42° C.

In one aspect, the reaction is carried out by adding 0.01 to 5 equivalents of said Lewis acid to 1.0 equivalent of said chiral 1,3-diol. In a further aspect, 0.5 to 2.0 equivalents of said Lewis acid is added.

Some of the compounds of Formula V have asymmetric centers where the stereochemistry is unspecified and the diastereomeric mixtures of these compounds are included as well as the individual stereoisomers when referring to a compound of Formula V generally.

Additionally, methods and salt forms are described that enable isolation and purification of the desired isomer.

Definitions

In accordance with the present invention and as used herein, the following terms are defined with the following meanings, unless explicitly stated otherwise.

The term "hexanes" refers to commercially available HPLC reagent solutions which contains approximately 95% hexane, methylcyclopropane, and methylpentane.

The term "dialkyl" refers to a compound containing two alkyl groups. The term "alkyl" refers to saturated aliphatic groups including straight-chain, branched chain and cyclic groups. Suitable alkyl groups include methyl, ethyl, isopropyl, and cyclopropyl.

The term "alkylene" refers to a divalent straight chain, branched chain or cyclic saturated aliphatic group. In one aspect the alkylene group contains up to and including 10 atoms. In another aspect the alkylene chain contains up to and including 6 atoms. In a further aspect the alkylene groups contains up to and including 4 atoms. The alkylene group can be either straight, branched, unsaturated, or cyclic. The alkylene may be optionally substituted with 1-3 substituents.

The term "aryl" refers to aromatic groups which have 5-14 ring atoms and at least one ring having a conjugated pi electron system and includes carbocyclic aryl, heterocyclic aryl and biaryl groups, all of which may be optionally substituted.

Heterocyclic aryl or heteroaryl groups are groups which have 5-14 ring atoms wherein 1 to 4 of the ring atoms are heteroatoms with the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, adeninyl, thyminyl, cytosinyl, guaninyl, uracilyl, and the like, all optionally substituted.

The term "monocyclic aryl" refers to aromatic groups which have 5-6 ring atoms and includes carbocyclic aryl and heterocyclic aryl. Suitable aryl groups include phenyl, furanyl, pyridyl, and thienyl. Aryl groups may be substituted.

The term "monocyclic heteroaryl" refers to aromatic groups which have 5-6 ring atoms wherein 1 to 4 heteroatoms are ring atoms in the aromatic ring and the remainder of the ring atoms being carbon atoms. Suitable heteroatoms include oxygen, sulfur, and nitrogen.

The term monovalent nitrogen protecting group refers to a protecting group that is attached to nitrogen by a single bond. Examples include but are not limited to tert-butyloxycarbonyl, benzyloxycarbonyl, trifluoroacetyl and benzyl.

The term divalent nitrogen protecting group refers to a protecting group that is attached to nitrogen either by two single bonds or by a double bond. Examples include but are not limited to phthalimidoyl, phenylmethylidene, dimethylaminomethylidene and diethylaminomethylidene.

The term "optionally substituted" or "substituted" includes aryl groups substituted by one to four substituents, independently selected from lower alkyl, lower aryl, and halogens. In one aspect these substituents are selected from the group consisting of halogens.

The term 'chiral' refers to an object or molecule that is not superimposable upon its mirror image.

The term 'diastereoselective' refers to a reaction in which two or more diastereomers may be formed wherein unequal amounts of the diastereomers are obtained. If two diastereomers are formed, typically the ratio of diastereomers is at least 2:1.

The term 'Lewis acid' refers to any species that can accept a pair of electrons and form a coordinate covalent bond.

The term "cis" stereochemistry refers to the relationship of the V group and M group positions on the six-membered ring. V and M are said to be located cis to each other if they lie on the same side of the plane. The formula below shows a cis stereochemistry.

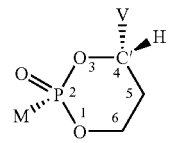

Another cis stereochemistry would have V and M pointing above the plane. The formula below shows this cis stereochemistry.

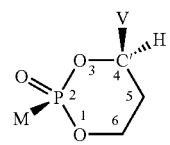

The term "trans" stereochemistry refers to the relationship of the V group and M group positions on the six-membered ring. V and M are said to be located trans to each other if they lie on opposite side of the plane. The formula below shows a trans stereochemistry.

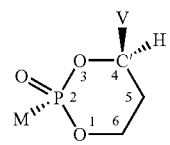

Another trans stereochemistry would have M pointing above the plane and V pointing below the plane. The formula below shows this trans stereochemistry.

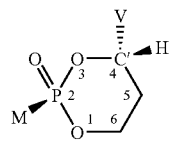

The term "N6-substituted" refers to the substitution at the amine attached at the 6-position of a purine ring system. N6- is generally substituted with an amine protecting group. Examples include the dialkylaminomethylene group, BOC, CBz, trityl as well as divalent groups like phthalimidoyl.

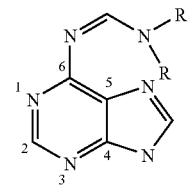

The terms "N,N-dialkylaminomethyleneimine," "N,N-dialkylaminomethylene" and "N,N-dialkylaminomethylidene" refer to the functional group or substitution of the following structure

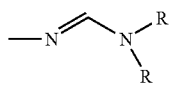

wherein R groups include but are not limited to C1-C4 acyclic, alkyl, C5-C6 cyclic alkyl, benzyl, phenethyl, or R groups together form piperdine, morpholine, and pyrrolidine.

The term "nitrogen protecting group" refers to R group and includes but is not limited to BOC, CBz, trityl, N,N-dialkylaminomethylidene, phthalimidoyl, or other monovalent and divalent groups.

The term "phosphonic acid halide" refers to a phosphonic acid wherein the two OH groups have been replaced by halogen atoms. The formula below shows this structure

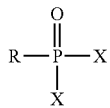

The term "phosphonic acid anhyride" refers to a compound that is formed by combining two moles of phosphonic acid with the removal of one mole of water. The formula below shows an example of this structure

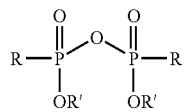

The term "phosphonic acid carbonate" refers to a phosphonic acid wherein one OH groups has been replaced by a carbonate group. The formula below shows an example of this structure

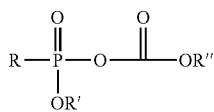

The term "percent enantiomeric excess (% ee)" refers to optical purity. It is obtained by using the following formula:

$$\frac{[R]-[S]}{[R]+[S]} \times 100 = \% R - \% S$$

where [R] is the amount of the R isomer and [S] is the amount of the S isomer. This formula provides the % ee when R is the dominant isomer.

The term "d.e." refers to diastereomeric excess. It is obtained by using the following formula:

$$\frac{[cis]-[trans]}{[cis]+[trans]} \times 100 = \% [cis] - \% [trans]$$

The term "diastereoisomer" refers to compounds with two or more asymmetric centers having the same substituent groups and undergoing the same types of chemical reactions wherein the diasteroismers have different physical properties, have substituent groups which occupy different relative positions in space, and have different biological properties.

The term "racemic" refers to a compound or mixture that is composed of equal amounts of dextrorotatory and levorotatory forms of the same compound and is not optically active.

The term "enantiomer" refers to either of a pair of chemical compounds whose molecular structures have a mirror-image relationship to each other.

The term "halogen" refers to chloride, bromide, iodide, or fluoride.

The term "prodrug" as used herein refers to any M compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g., HO—, HS—, HOOC—, $R_2N$—, associated with the drug that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of formula A, fall within the scope of the present invention. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. The biologically active compounds

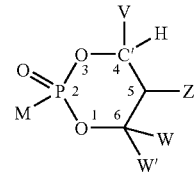

Formula A include, for example, anticancer agents, and antiviral agents.

The term "cyclic phosphate ester of 1,3-propanediol", "cyclic phosphate diester of 1,3-propanediol", "2 oxo $2\lambda^5$[1,3,2]dioxaphosphorinane", "2-oxo-[1,3,2]-dioxaphosphorinane", or "dioxaphosphorinane" refers to the following:

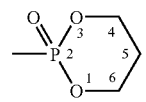

The term "enhancing" refers to increasing or improving a specific property.

The term "enriching" refers to increasing the quantity of a specific isomer produced by a reaction.

The term "non-nucleophilic inorganic base" refers to an inorganic base that has low potential to react with electrophiles. Examples of non-nucleophilic inorganic bases include sodium bicarbonate, sodium carbonate, and potassium carbonate.

The term "activated phosphonic acid" refers to a phosphonic acid wherein the two OH groups have been replaced by leaving groups, such as halogen atoms.

The following well known chemicals are referred to in the specification and the claims. Abbreviations and common names are also provided.

BOC; tert-butoxycarbonyl group
CBz; benzyl carbamate
Trityl; triphenylmethyl group
CH$_2$Cl$_2$; dichloromethane or methylene chloride
DCM; dichloromethane
(−)-DIP-Cl; (−)-β-chlorodiisopinocampheylborane
DMAP; 4-dimethylaminopyridine
DMF; dimethylformamide
HCl; hydrochloric acid
KI; potassium iodide
MgSO$_4$; magnesium sulfate
MTBE; t-butyl methyl ether
NaCl; sodium chloride
NaOH; sodium hydroxide
PyBOP; benzotriazol-1-yloxytripyrrolidinophosphonium hexafluorophosphate
TEA; triethylamine
THF; tetrahydrofuran
TMSCl; chlorotrimethylsilane
TMEDA; tetramethylethlenediamine
EDTA; ethylenediaminetetraacetic acid.

The following well known drugs are referred to in the specification and the claims. Abbreviations and common names are also provided.

PMEA; 9-(2-phosphonylmethoxyethyl)adenine (Adefovir)
(R)-PMPA; (R)-9-(2-phosphonylmethoxypropyl)adenine (Tenofovir)
(R)-PMPDAP; (R)-9-(2-phosphonylmethoxypropyl)-2,6-diaminopurine
FPMPDAP; 9-[(2RS)-3-fluoro-2-phosphonylmethoxypropyl]-2,6-diaminopurine
FPMGP; 9-[(2RS)-3-fluoro-2-phosphonylmethoxypropyl]guanine
(S)-HPMPDAP; 9-=[2S]-3-hydroxy-2-phosphonylmethoxylpropyl]-2,6-diaminopurine
PMEG; 9-(2-phosphonylmethoxyethyl)guanine
PMEI; 2-phosphonylmethoxyethyl-6-oxopurine
PMEMAP; 9-(2-phosphonylmethoxyethyl)2-aminopurine
PMET; 2-phosphonylmethoxyethyl-thymine

DETAILED DESCRIPTION OF THE INVENTION

This invention is directed to the discovery that the utilization of Lewis acid catalysis in the coupling process during the synthesis of cyclic 1,3-propanyl esters of phosphonyl compounds enhanced the ratio of diastereomers of the resultant product. In one aspect the invention is directed towards the utilization of Lewis acid catalysis in the coupling process during the synthesis of cyclic 1-aryl-1,3-propanyl esters of phosphonyl compounds. Compounds synthesized by the process of the present invention are directed towards cyclic esters of phosphonic acids as shown in the following formula:

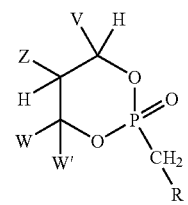

Formula W

Cyclic ester prodrugs of phosphonic acids have been demonstrated to be useful in improving the oral bioavailability of drugs containing a phosphonic acid moiety, and in increasing the concentration of the active drug in the liver (U.S. Pat. No. 6,312,662). The cyclic 1,3-propanyl-1-aryl phosphonate cyclic esters of PMEA and related analogs having cis relative stereochemistry have been shown to be able to treat diseases of the liver (U.S. PreGrant Published Application 2003/0229225 A1). These compounds enhance the oral delivery and/or prolong the pharmacodynamic half-life of PMEA and like analogs. In addition, the compounds achieve targeted delivery of PMEA to the liver and increase the therapeutic index of the drug.

The aforementioned prodrugs have been made in a modestly stereoselective manner by coupling a chiral 1,3-diol with a phosphonic acid dichloridate at low temperature (U.S. PreGrant Published Application 2003/0225277 A1). The dichloridate of PMEA is readily prepared using standard chlorination conditions. The coupling reaction with the dichloridate at low temperature was complicated by the poor solubility of the dichloridate. It was found that by adding a protected form of the dichloridate to the diol at low temperatures a diastereoselectivity of 50% could be achieved.

Lewis acids have been used to improve the diastereoselectivity of chemical reactions. For example, titanium tetrachloride has been used to enhance the diastereoselectivity of enolate aldol reactions (Evans et. al., *J. Am. Chem. Soc.* 112: 8215 (1990); Evans et. al., *J. Am. Chem. Soc.* 113: 1047 (1991)). It has been proposed that a six membered transition state is the controlling factor of the enhanced diastereoselectivity. It has also been shown that titanium tetrachloride can be used as a catalyst for phosphoryl transfer (Jones et. al., *Org. Lett.* 4: 3671 (2002)). However, Lewis acids have not been reported to improve the diastereoselectivity of formation of cyclic phosphonic esters; this application describes such an invention.

During the coupling reaction functional groups on the R as shown in the above Formula W, such as amines and hydroxyl groups, may be protected with a variety of amine protecting groups. An example of use of the dialkylamine methylidene group (N,N-dialkylaminomethylene and N,N-dialkylaminomethylidene) is shown below with the nitrogen attached to the carbon labeled 6 protected in the structure below.

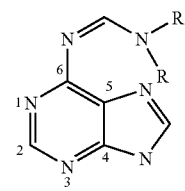

The process for the synthesis of cyclic 1,3-propanyl esters with the desired stereochemistry is via a convergent synthetic sequence. The final resultant compound contained two stereocenters, (1) the methine carbon which is identified as C4' in the steroisomeric structures and (2) the phosphorus of the cyclic phosphonate ring.

The phosphorus chirality was the result of the diastereoselective coupling of the parent phosphonic acid and the chiral diol. The desired cis isomer, wherein cis refers to the isomeric relationship between the phosphorus-carbon bond and the carbon-aryl bond of the cyclic phosphonate ring, was isolated via a selective crystallization of the acid salt.

Compounds Prepared by the Invention

1. Synthesis of N6-Protected PMEA-Dichloridate:

Chlorination of PMEA is achieved using oxalyl chloride and N,N-diethylformamide to give N6 protected-PMEA-dichloridate. N,N-dialkylformamide used in the chlorination step not only forms a Vilsmeyer chlorinating agent, but also protects the $NH_2$ group at the 6 position.

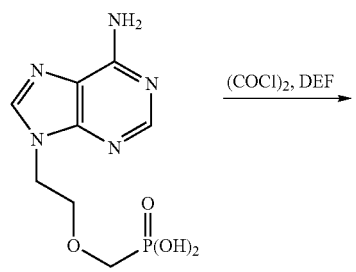

2. Coupling of Phosphonic Dichloridate and Chiral Diol:

2.1 Effect of Dichloridate Addition Order and Temperature.

Earlier work (U.S. Pat. No. 2003225277 A1) had shown that the coupling of the protected phosphonic acid dichloridate and diol can be accomplished by low temperature addition to the diol in the presence of base. This led to a modest d.e. of 50% and required conducting the reaction at low temperatures.

Unexpectedly and surprisingly, the inventors observed improved d.e.'s when this low temperature coupling was done in the presence of a Lewis acid. Changes were made to the order of addition of the reagents (see Table 1). When the solution of the diol and base was added to a mixture of the dichloridate and Lewis acid, the results were similar to those obtained above. When a complex of the diol and Lewis acid was added to the dichloridate, there was a further increase in both the d.e. and overall yield of the desired product. These results show that high diastereoselectivity is possible independent of addition order but that in one aspect the diol and Lewis acid are added to the dichloridate for high diastereoselectivity.

Another aspect found was that using this procedure, the coupling reaction no longer has to be performed at low temperatures.

TABLE 1

EFFECT OF SOLUTION COMPONENTS, TEMPERATURE AND ADDITION ORDER

| Entry | Base | Equiv. | Temp (° C.) | Addition | Cis:Trans Area % | d.e. |
|---|---|---|---|---|---|---|
| 1 | $Bu_3N$ | 4.8 | −70 to −65 | dichloridate to (diol + base + $TiCl_4$) | 59:13 | 64 |
| 4 | $Et_3N$ | 4.8 | −70 to −65 | dichloridate to (diol + base + $TiCl_4$) | 73:15 | 66 |
| 5 | $Et_3N$ | 3.1 | 10 to 15 | dichloridate to (diol + $TiCl_4$ + base) | 38:7 | 69 |
| 6 | $Et_3N$ | 4.0 | 0 to 10 | dichloridate to (diol + $TiCl_4$ + base) | 22:1 | 87 |
| 2 | $Bu_3N$ | 4.8 | 0 to 10 | (diol + base) to (dichoridate + $TiCl_4$) | 58:11 | 68 |
| 3 | $Et_3N$ | 4.8 | 0 to 10 | (diol + base) to (dichoridate + $TiCl_4$) | 60:14 | 62 |
| 7 | $Et_3N$ | 4.0 | 20 to 25 | (diol + $TiCl_4$ + base) to dichloridate | 76:1 | 97 |
| 8 | $Et_3N$ | 4.0 | Reflux | (diol + $TiCl_4$ + base) to dichloridate | 76:6 | 85 |
| 9 | Hunig | 4.0 | 18 to 22 | (diol + $TiCl_4$ + base) to dichloridate | 73:4 | 90 |
| 10 | $Et_3N$ | 6.0 | 17 to 19 | (diol + $TiCl_4$ + base) to dichloridate | 73:3 | 92 |
| 11 | $Et_3N$ | 9.0 | 17 to 22 | (diol + $TiCl_4$ + base) to dichloridate | 74:2 | 95 |

-continued

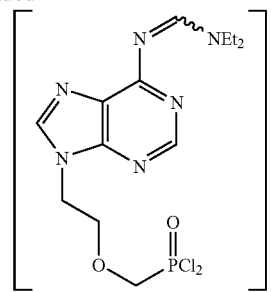

3. Isolation of Cyclic Phosphonic Ester:

The reaction mixture from the coupling reaction was quenched with methanol and partitioned with water. The acidic aqueous phase containing the product was extracted several times with chloroform. The combined organic layers were dried and concentrated to an oil, affording the N6 protected form of the cyclic phosphonic ester.

An alternative method of isolation consists of addition of a base (such as triethylamine) to the reaction mixture, resulting in precipitation of salts derived from the Lewis acid. Filtration of the precipitated material is facilitated by the use of a filter aid (e.g. diatomaceous earth, Fuller's earth, Montmorillonite clay), after which the filtrate containing the product is concentrated or further manipulated in the usual way (washing with water, extraction of the product into aqueous acid, back-extraction with an organic solvent, etc.).

A further aspect of workup involves use of a chelating agent to remove materials derived from the Lewis acid. In one aspect the chelating agent could be a bifunctional organic compound (e.g., TMEDA, tartaric acid, EDTA) that renders the salts derived from the Lewis acid water-soluble, and hence removable by extraction. In another aspect the chelating agent could also be a functionalized solid support (e.g., a polymeric resin containing amine or carboxylic acid functional groups capable of chelation), in which case removal of salts is accomplished by filtration.

4. Crystallization of cis Prodrug Salt:

Deprotection of the N6 position of the coupled phosphonic acid and chiral diol is accomplished under mild acidic conditions. The isolated coupling mixture was treated with refluxing acetic acid in ethanol to effect nitrogen deprotection. Crystallization of the resultant product using methanesulfonic acid gave rise to the cis prodrug as a mesylate salt (Formula C) with 94-98% chemical purity. The trans isomer is the major impurity and a second crystallization of the final material from an alcohol such as methanol gave greater than 96% diastereomeric purity (d.e. from 96 to 99%).

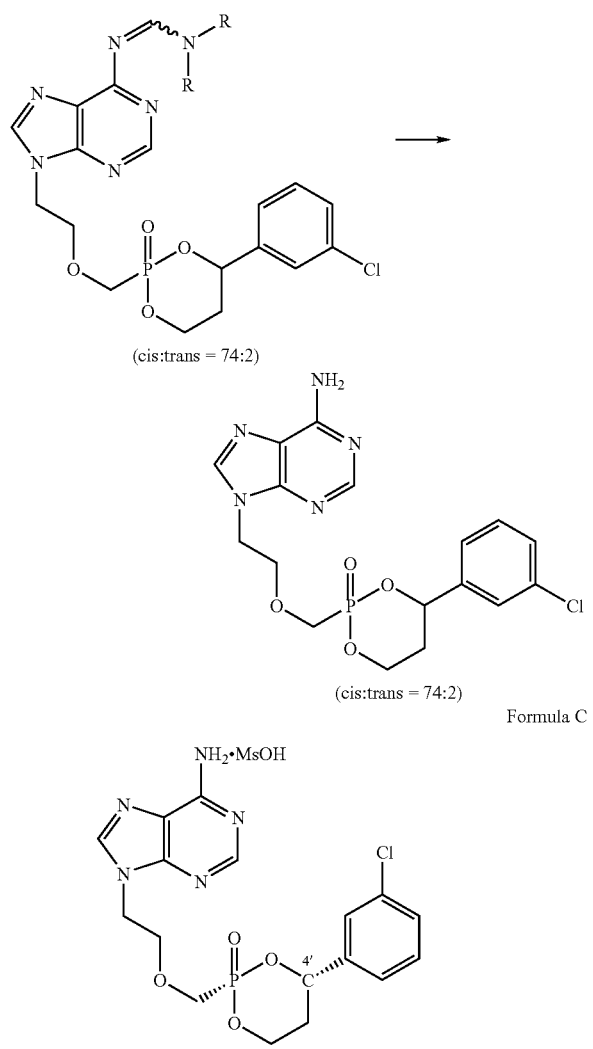

The use of other acids including but not limited to such as sulfuric, nitric, hydrochloric, phosphoric, sulfonic, tartaric, citric, maleic, malic, malonic, lactic, oxalic acids and the like, may lead to better recovery and isomeric ratio of the product. The protocol as described for PMEA is also applicable to other PME or PMP derivatives.

The compounds used in this invention and their preparation can be understood further by the examples which illustrate some of the processes by which these compounds are prepared. These examples should not however be construed as specifically limiting the invention and variations of the compounds, now known or later developed, are considered to fall within the scope of the present invention as hereinafter claimed.

EXAMPLES

Example 1

Preparation of 3-(3-chlorophenyl)-3-oxo-propanoic acid (1)

The diol was prepared as described in U.S. PreGrant Published Application No. 20030225277A1. A 12 L, 3-neck round bottom flask was equipped with a mechanical stirrer and addition funnel (2 L). The flask was flushed with nitrogen and charged with diisopropylamine (636 mL) and THF (1.80 L). The stirred contents were cooled to −20° C. n-Butyllithium (1.81 L of a 2.5 M solution in hexanes) was added slowly with stirring, and the temperature was maintained between −20 and −28° C. After the addition was complete (30 min), the addition funnel was rinsed with hexanes (30 mL) and the stirred solution was then cooled to −62° C. Trimethylsilyl acetate (300 g) was added slowly with stirring, maintaining the temperature at <−60° C. After the addition was complete (about 30 min), the solution was stirred at −60° C. for 15 min. 3-Chlorobenzoyl chloride (295 mL) was added slowly with stirring, maintaining the temperature at <−60° C. After the addition was complete (about 65 min), the cooling bath was removed and the reaction solution was stirred for approximately 1.25 h, with gradual warming to 0° C. The reaction flask was cooled with an ice bath, then water (1.8 L) was added to the stirred solution. The reaction mixture was stirred for 10 min, and then diluted with t-butyl methyl ether (MTBE) (1.0 L). The lower aqueous phase was separated and transferred to a round bottom flask equipped with a mechanical stirrer. MTBE was added (1.8 L) and the stirred mixture was cooled to <10° C. in an ice bath. Concentrated HCl solution (300 mL of 12 M solution) was added and the mixture was vigorously stirred. The layers were separated and the aqueous phase was further acidified with concentrated HCl (30 mL) and extracted again with MTBE (1.0 L). The combined MTBE extracts were washed with approximately 10% NaCl solution (1 L), dried (MgSO$_4$, 70 g), filtered and concentrated under reduced pressure to give 827 g of a yellow solid. The crude solid was slurried in hexanes (2.2 L) and transferred to a round bottom flask equipped with a mechanical stirrer. The mixture was stirred at <10° C. for 1 h, then filtered, washed with hexanes (4×100 mL) and dried to constant weight (−30 in. Hg, ambient temperature, 14 h).

Example 2

Preparation of (S)-3-(3-Chlorophenyl)-3-hydroxypropanoic acid (2)

The 3-hydroxypropanoic acid was prepared as described in U.S. PreGrant Published Application No. 20030225277A1. A 12 L, 3-neck round bottom flask was equipped with a mechanical stirrer and addition funnel (1 L). The flask was flushed with nitrogen and charged with 3-(3-chlorophenyl)-3-oxo-propanoic acid (275.5 g) 1 and dichloromethane (2.2 L). A thermocouple probe was immersed in the reaction slurry and the stirred contents were cooled to −20° C. Triethylamine (211 mL) was added over 5 min. to the stirred slurry and all solids dissolved. A dichloromethane solution of (−)-beta-chlorodiisopinocampheylborane (1.60 M, 1.04 L) was charged to the addition funnel, and then added slowly with stirring while maintaining the temperature between −20 and −25° C. After the addition was complete (approximately 35 min), the solution was warmed to ice bath temperature (2-3° C.) and stirred. After approximately 4 h of stirring an in-process NMR analysis indicated the starting material 1 was <4%.

The residual starting material 1 was measured by proton NMR as follows: removing a 0.5 mL sample of the reaction mixture and quenching with water (0.5 mL) and 3 M NaOH solution (0.5 mL). The quenched mixture was stirred and the layers separated. The aqueous phase was acidified with 2 M HCl (1 mL) and extracted with ethyl acetate (1 mL). The organic phase was separated, filtered through a plug of MgSO$_4$ and concentrated with a stream of nitrogen. The residue was dissolved in CH$_2$Cl$_2$ and the solvent was evaporated with a stream of nitrogen. Water (1.2 L) was added to the cloudy orange reaction mixture, followed by 3 M NaOH solution (1.44 L). The mixture was vigorously stirred for 5 min. and then transferred to a separatory funnel. The layers were separated and the basic aqueous phase was washed with ethyl acetate (1 L). The aqueous phase was acidified with concentrated HCl (300 mL) and extracted with ethyl acetate (2 times with 1.3 L each). The two acidic ethyl acetate extracts were combined, washed with approximately 10% NaCl solution (600 mL), dried with MgSO$_4$ (130 g), filtered and concentrated under reduced pressure to provide 328 g of a yellow oil. The oil crystallized upon standing. The resulting solid was slurried in ethyl acetate (180 mL) and transferred to a 2 L, 3-neck round bottom flask, equipped with a mechanical stirrer. The stirred ethyl acetate mixture was cooled to <10° C. (ice bath), then diluted with hexanes (800 mL). The resulting mixture was stirred at ice bath temperature for 4 h, and then filtered. The collected solid was washed with 4:1 hexanes:ethyl acetate (3×50 mL) and dried to constant weight (−30 inches of Hg, ambient temperature, 12 h).

Example 3

Preparation of (S)-(−)-1-(3-chlorophenyl)-1,3-propanediol (3)

The diol was prepared as described in U.S. PreGrant Published Application No. 20030225277 A1. A 12 L, 3-neck round bottom flask was equipped with a mechanical stirrer, addition funnel (2 L) and thermometer. The flask was flushed with nitrogen and charged with (S)-3-(3-chlorophenyl)-3-hydroxypropanoic acid 2 (206.7 g) and THF (850 mL), and the stirred solution was cooled to 5° C. (ice bath). A 1 M borane in THF solution (2.14 L) was charged to the addition funnel, and then added slowly with stirring maintaining the temperature at <10° C. After the addition was complete (approximately 1 h), the cooling bath was removed and the solution was stirred at ambient temperature for 1 h. The reaction solution was slowly and cautiously quenched with water (600 mL), followed by 3 M NaOH solution (850 mL). The mixture was stirred for 10 min. with an observed temperature increase to approximately 40° C., and then the mixture was transferred to a separatory funnel. The layers were separated and the aqueous phase was extracted again with ethyl acetate (600 mL). The combined organic phase was washed with approximately 10% NaCl solution (500 mL), dried (MgSO$_4$, 322 g), filtered and concentrated under reduced pressure to provide 189.0 g of a pale yellow oil (101%).

Example 4

Preparation 9-{2-[2,4-cis-(S)-(+)-4-(3-chlorophenyl)-2-oxo-1,3,2-dioxaphosphorinan-2-yl]methoxyethyl}adenine methanesulfonate (9)

Example 4.1

Formation of Dichloridate (8)

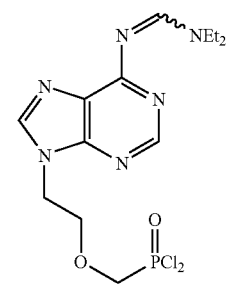

8

A 250 mL, 4-neck round bottom flask was equipped with a mechanical stirrer, condenser, addition funnel (25 mL) and heating mantle. The flask was flushed with nitrogen and charged with PMEA (15.05 g), dichloromethane (190 mL) and N,N-diethylformamide (6.15 g). Oxalyl chloride (15.3 mL) was charged to the addition funnel, and added slowly to the stirred reaction mixture at a rate to maintain control over gas evolution (0.5 h.). After the addition was complete (30 min.), the addition funnel was removed and the vigorously stirred mixture was heated at reflux for 4 h.

Example 4.2

Coupling Reaction

A 250 mL, 3-neck round bottom flask was equipped with a mechanical stirrer, a cooling bath, nitrogen inlet, thermocouple, and addition funnel (25 mL). The flask was flushed with nitrogen and charged with (S)-(−)-(3-chlorophenyl)-1,3-propanediol 3 (10.6 g) and methylene chloride (150 mL). The solution was cooled to <10° C. Titanium tetrachloride (6.2 mL) was added and a heavy precipitate formed after approximately 5 min. Triethylamine (31 mL) was added, the precipitate dissolved, and the solution turned purple. After a few additional minutes a light precipitate formed. The diol solution containing the titanium tetrachloride was added to the dichloridate solution 8 over a 90 min. period. The initial temperature was 19° C. and the final temperature was 24° C. The reaction was stirred at ambient temperature for 1 h and then quenched with methanol (90 mL). The in situ yield of the cis coupled product was 91%. The reaction mixture was washed with water (165 mL) and the layers were separated. The aqueous phase was extracted with chloroform (3×150 mL). The combined organic phases were washed with 5% sodium chloride (300 mL). The resultant brine layer contained additional product and was extracted with chloroform (6×50 mL). The combined organic phase was dried (MgSO₄, 35 g), filtered through diatomaceous earth (Celite 521), and concentrated under reduced pressure to give an oil. The HPLC analysis samples were dissolved in methanol.

HPLC Conditions: YMC-Pack R & D, R-33-5 S-5 120A, 250×4.6 mm; mobile phase: Solvent A=20 mM potassium phosphate, pH 6.2; Solvent B=acetonitrile; gradient: 10-60% B/15 min., 60-10% B/2 min., 10% B/3 min.; 1.4 mL/min.; inj. vol.=10 μL; UV detection at 270 nm. Retention times: cis 13=12.5 min., trans 14=13.0 min.

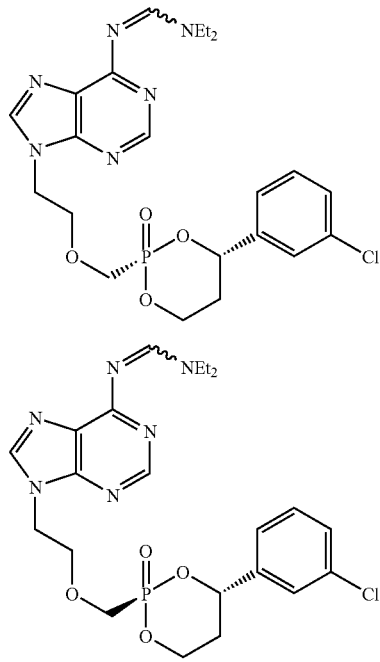

The material was dissolved in ethanol (150 mL) and transferred to a 500 mL round bottom flask equipped with magnetic stirring, condenser and heating mantle. Acetic acid (16.5 mL) was added and the solution was heated at reflux for 8 h. HPLC indicated the reaction was complete. The HPLC samples were dissolved in methanol.

HPLC Conditions: YMC-Pack R & D, R-33-5 S-5 120A, 250×4.6 mm; mobile phase: Solvent A=20 mM potassium phosphate, pH 6.2; Solvent B=acetonitrile; gradient: 10-60% B/15 min., 60-10% B/2 min., 10% B/3 min.; 1.4 mL/min.; inj. vol.=10 μL; UV detection at 270 nm. Retention times: cis 15=9.5 min., trans 16=9.8 min.

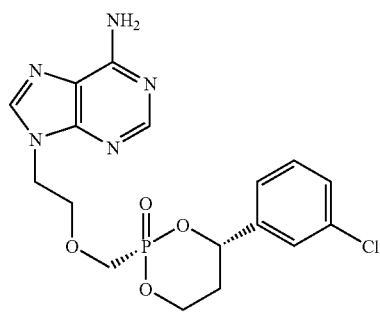

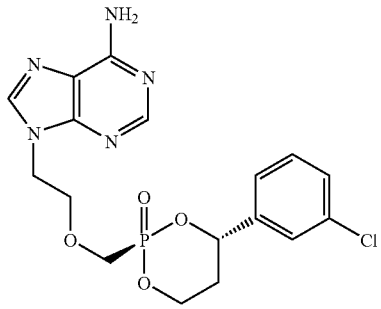

Example 4.3

Crystallization of 9-{2-[$2,4$-cis-(S)-(+)-4-(3-chlorophenyl)-2-oxo-1,3,2-dioxaphosphorinan-2-yl]methoxyethyl}adenine methanesulfonate (9)

Methanesulfonic acid (9.03 g) was added and a precipitate formed after 15 min. The mixture was diluted with ethanol (90 mL) and heated until all solids dissolved (pot temperature=78° C.). The solution was cooled with stirring and a precipitate formed at 50° C. The resulting mixture was stirred for 4 h, with cooling to ambient temperature, then at ice bath temperature for 1 h. The mixture was filtered and the collected solid was washed with cool ethanol (2×10 mL) and dried to constant weight (−30 in. Hg, 40-50° C., overnight) to yield a pale yellow solid. Recovery=19.9 g 9 (70%). The solid cis: trans ratio was 97.8:1.7.

Chiral HPLC: Pirkle covalent (S,S) Whelk-O 1 10/100krom FEC 250×4.6 mm; mobile phase=55:45, methanol: 0.1% HOAc in water; isocratic; 1.0 mL/min.; inj. Vol.=10 μL; UV detection at 260 nm; sample preparation=2.0 mg/mL in water. Retention times: cis-(R)5=24.6 min., trans-(R) 6=27.5 min., cis-(S) 7=18.0 min.

¹H NMR (D₂O) was used to confirm structure of components.

Example 4.4

Recrystallization of 9-{2-[2,4-cis-(S)-(+)-4-(3-chlorophenyl)-2-oxo-1,3,2-dioxaphosphorinan-2-yl]methoxyethyl}adenine methanesulfonate (9)

A 1 L, 3-neck round bottom flask was equipped with a mechanical stirrer, condenser, heating mantle and thermometer. The flask was charged with the crude mesylate salt 9 and ethanol (400 mL). The stirred mixture was heated at reflux (pot temperature was 78° C.) until all solids dissolved (approximately 10 min.). The stirred mixture was gradually cooled to ambient temperature over 3 h (a precipitate formed at 52° C.). The mixture was stirred at ambient temperature for an additional hour, cooled to 10° C. and stirred for another hour and then filtered. The collected solid was washed with cool ethanol (2×10 mL) and dried overnight (–30 in Hg, 45-50° C., 16 hrs.).) to yield a pale yellow solid (17.64 g, 62% overall yield). Cis:trans ratio=99.5:0.5. Color: pale yellow solid

Example 5

Coupling of iodomethylphosphonic acid with (S)-(–)-1-(3-chlorophenyl)-1,3-propanediol A 500 mL 4-neck round bottom flask equipped with a heating mantle, mechanical stirring, an addition funnel, thermocouple, and a condenser with nitrogen inlet was charged with methylene chloride (80 mL), iodomethylphosphonic acid (9.88 g, 44.5 mmol), and N,N-diethylformamide (0.4 mL, 5.0 mol). The oxalyl chloride (9.0 mL, 103 mmol) was added via the addition funnel at such a rate as to maintain control over the gas evolution (0.25 h). The slurry was heated to reflux for 4 h during which time all of the solids had dissolved. The solution was cooled to room temperature. A 100 mL 3-neck round bottom flask equipped with a cooling bath, mechanical stirring, nitrogen inlet, thermocouple, and tubing adapter was charged with methylene chloride (70 mL), S(–)-1-(3-chlorophenyl)-1,3-propanediol 3 (8.85 g, 44.6 mmol). The solution was cooled to <10° C. Titanium tetrachloride (4.9 ml, 45.6 mmol) was added, and a heavy precipitate formed after approximately 5 min. Triethylamine (25 ml, 178 mmol) was added. The precipitate dissolved, and the solution turned to a purple color. After a few minutes, a light precipitate was observed forming. The diol/titanium tetrachloride solution was added to the dichloridate solution over 15 min; the initial temperature was 20° C. and the final temperature was 25° C. The reaction was stirred at ambient temperature for 1 h, and then quenched with methanol (10 mL) and water (50 mL). After separation of layers, the aqueous phase was extracted with methylene chloride (50 mL). The combined organic layers were dried over MgSO$_4$, and concentrated to an oil (20 g). The ratio of major to minor isomer=3.62:1.00. by $^{31}$P NMR (DMSO) δ=91.0 (3.62 P), 88.6 (1.00P).

Example 6

Preparation of 4-{4-[2,4-cis-(S)-4-(3-chlorophenyl)-2-oxo-2λ$^5$-[1,3,2]dioxaphosphinan-2-ylmethoxy]-2,6-dimethylbenzyl}-2-isopropylphenol A 500 ml 4-neck round bottom flask equipped with a heating mantle, mechanical stirring, an addition funnel, thermocouple, and a condenser with nitrogen inlet is charged with methylene chloride (190 ml), [4-(3-isopropyl-4-triisopropyl-silanyloxy-benzyl)-3,5-dimethyl-phenoxymethyl]-phosphonic acid (55.1 mmol), and N,N-diethylformamide (5 mmol). Oxalyl chloride (115 mmol) is added via the addition funnel at a rate to control the gas evolution (0.5 h). The slurry is heated to reflux for 4 h. The solution is cooled to room temperature. A 250 ml 3-neck round bottom flask equipped with a cooling bath, mechanical stirring, nitrogen inlet, thermocouple, and tubing adapter is charged with methylene chloride (150 ml) and S(–)-1-(3-chlorophenyl)-1,3-propanediol (55.1 mmol). The solution is cooled to <10° C. Titanium tetrachloride (56.0 mmol) is added, and a heavy precipitate forms after approximately 5 min. Triethylamine (222 mmol) is added. The precipitate dissolves, and the solution changes to a purple color. After a few minutes, a light precipitate forms. The diol/titanium tetrachloride solution is added to the dichloridate solution over 90 min. The reaction is stirred at ambient temperature for 1 h, and then is quenched with methanol (90 ml). The cis:trans ratio is approximately 3 to 1. The solution is poured into water (165 ml). The mixture is transferred to a separatory funnel, and the layers are separated. The organic phase is washed with 5% sodium chloride solution (300 ml) and is dried over MgSO$_4$. The methylene chloride is removed by vacuum distillation. THF (300 ml) and tetrethylammonium fluoride (56 mmol) is added. The solution is stirred for 1 h followed by quenching with water (50 ml). After separation of layers, the aqueous phase is extracted with ethyl acetate (50 ml). The combined organic layers are washed with brine (50 ml), dried over MgSO$_4$, and are concentrated. The product, 4-{4-[2,4-cis-(S)-4-(3-chlorophenyl)-2-oxo-2λ$^5$-[1,3,2]dioxaphosphinan-2-ylmethoxy]-2,6-dimethylbenzyl}-2-isopropylphenol is purified by crystallization or chromatography.

Example 7

Preparation of 4-{4-[2,4-cis-(S)-4-(3,5-dichlorophenyl)-2-oxo-2λ$^5$-[1,3,2]dioxaphosphinan-2-ylmethoxy]-2,6-dimethylbenzyl}-2-isopropylphenol A 500 ml 4-neck round bottom flask equipped with a heating mantle, mechanical stirring, an addition funnel, thermocouple, and a condenser with nitrogen inlet is charged with methylene chloride (190 ml), [4-(3-isopropyl-4-triisopropyl-silanyloxy-benzyl)-3,5-dimethyl-phenoxymethyl]-phosphonic acid (55.1 mmol), and N,N-diethylformamide (5 mmol). Oxalyl chloride (115 mmol) is added via the addition funnel at a rate to maintain control over the gas evolution (0.5 h). The slurry is heated to reflux for 4 h. The solution is cooled to room temperature. A 250 ml 3-neck round bottom flask equipped with a cooling bath, mechanical stirring, nitrogen inlet, thermocouple, and tubing adapter is charged with methylene chloride (150 ml) and S(–)-1-(3,5-dichlorophenyl)-1,3-propanediol (55.1 mmol). The solution is cooled to <10° C. Titanium tetrachloride (56.0 mmol) is added, and a heavy precipitate forms after approximately 5 min. Triethylamine (222 mmol) is added. The precipitate dissolves, and the solution exhibits a color change to purple. After a few minutes, a light precipitate forms. The diol/titanium tetrachloride solution is added to the dichloridate solution over 90 min. The reaction is stirred at ambient temperature for 1 h, and then quenched with methanol (90 ml). The cis:trans ratio is approximately 3 to 1. The solution is poured into water (165 ml). The mixture is transferred to a separatory funnel, and the layers are separated. The organic phase is washed with 5% sodium chloride solution (300 ml) and dried over MgSO$_4$. The methylene chloride is removed by vacuum distillation. THF (300 ml) and tetraethylammonium fluoride (56 mmol) is added. The solution is stirred for 1 h, and is then quenched with water (50 ml). After separation of layers, the aqueous phase is extracted with ethyl acetate (50 ml). The combined organic layers are washed with brine (50 ml), dried over MgSO$_4$, and is concentrated. The product, 4-{4-[2,4-cis-(S)-4-(3,5-dichlorophenyl)-2-oxo-2λ$^5$-[1,3,2]dioxaphosphinan- 2-ylmethoxy]-2,6-dimethylbenzyl}-2-isopropylphenol is purified by crystallization or chromatography.

Example 8

Preparation of 8-Nitro-3-[2,4-cis-4-(3-chlorophenyl)-2-oxo-1,3,2-dioxaphosphorinanyl]quinoline

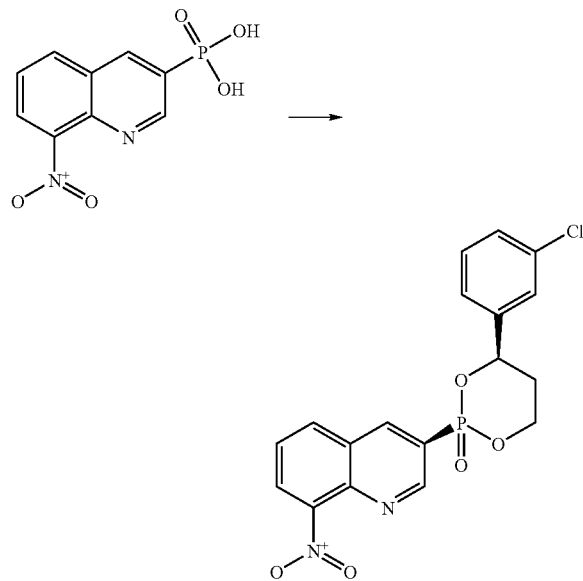

In a 250 mL r.b. flask, (15 mmol) of 8-nitroquinoline-3-phosphonic acid HBr salt suspended in 1,2-dichloroethane (50 mL) was combined with (37 mmol) oxalyl chloride and DMF (300 uL). The slurry was refluxed for 4 hrs then allowed to cool to rt. In a second r.b. flask, (15 mmol) of (3-chlorophenyl)-1,3-propanediol was dissolved in methylene chloride (40 mL) and cooled to −78° C. To this solution was added (15.2 mmol) of $TiCl_4$. After stirring for 5 min at 0° C., (60 mmol) of triethylamine was slowly added and the resulting mixture stirred for an additional 2 min. The diol mixture was added via addition funnel to the dichloridate solution over a period of 1 hr then allowed to stir at rt overnight. The reaction mixture was quenched by adding MeOH (20 mL), stirring for 20 min then combining with 10% aqueous tartaric acid solution. After stirring for 30 more min, TMEDA (20 mL) was added (exothermic!) followed by ice water and the layers separated. The aqueous portion was extracted with methylene chloride (2×100 mL), the organics combined, dried over $Na_2SO_4$ and concentrated under vacuum to afford the crude product. Flash chromatography ($SiO_2$) using DCM/MeOH (60:1 to 40:1) as the eluting gradient gave 3.3 g of product as a 25:1 cis/trans mixture. $^{31}P$ NMR (DMSO) δ=11.12 (cis), 7.19 (trans).

I claim:

1. A method for the diastereoselective preparation of compounds of Formula II:

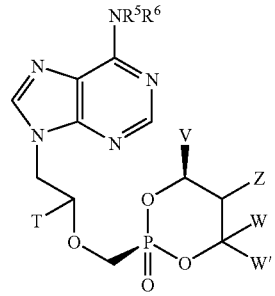

Formula II wherein:
V is selected from group consisting of aryl, and monocyclic heteroaryl, all optionally substituted with 1-4 substituents;

W and W' are independently selected from the group consisting of H, optionally substituted alkyl, optionally substituted alkenyl, optionally substituted alkynyl, optionally substituted monocyclic aryl, and optionally substituted monocyclic heteroaryl;

Z is selected from the group consisting of halogen, —CN, —$COR^3$, —$CONR^4_2$, —$CO_2R^3$, —$CHR^2OC(O)R^3$, —$CHR^2OC(S)R^3$, —$CHR^2OC(O)SR^3$, —$CHR^2OCO_2R^3$, —$OR^3$, —$SR^3$, —$R^2$, —$NR^3_2$, —$OCOR^3$, —$OCO_2R^3$, —$SCOR^3$, —$SCO_2R^3$, —$(CH_2)_p$—$OR^4$, and —$(CH_2)_p$—$SR^4$;

T is selected from the group consisting of H and lower alkyl;

$R^2$ is hydrogen or lower alkyl;

$R^3$ is alkyl;

$R^4$ is alkyl or acyl;

p is 2 or 3;

r is 0 or 1, and s is 0 or 1;

$R^5$ is a monovalent amine protecting group, and $R^6$ is hydrogen; or, $R^5$ and $R^6$ taken together are a divalent amine protecting group;

the method comprising:
combining a 1-(V)-1,3-propane diol with a compound of Formula III in the presence of a Lewis acid:

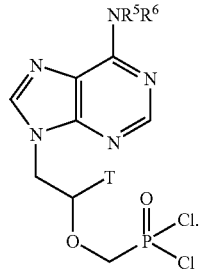

Formula III wherein the ratio of cis- to trans-diastereomers of the compounds of Formula II formed is greater than or equal to 3:1.

2. The method of claim 1 wherein said 1-(V)-1,3-propane diol is added to said Lewis acid and then the diol-Lewis acid complex is added to said compound of Formula III.

3. The method of claim 1 wherein said Lewis acid is selected from the group consisting of TiCl$_4$, BF$_3$, SnCl$_4$, SmI$_2$, and AlCl$_3$.

4. The method of claim 3 wherein said Lewis acid is TiCl$_4$.

5. The method of claim 1 wherein said Lewis acid is Ti(O-(C$_1$-C$_4$)alkyl)$_4$.

6. The method of claim 1 further comprising adding a base selected from the group consisting of tertiary alkyl amines, N-containing heterocyclic aromatic bases, and non-nucleophilic inorganic bases.

7. The method of claim 6 wherein said base is selected from the group consisting of triethylamme, tri(n-butyl)amine, pyridine, quinoline, and diisopropylethylamine.

8. The method of claim 1 wherein the temperature for the reaction is between −78° C. and 60° C.

9. The method of claim 8 wherein said temperature is between −20° C. and 50° C.

10. The method of claim 9 wherein said temperature is between 15° C. and 42° C.

11. The method of claim 1 further comprising:
adding 0.01 to 5 equivalents of said Lewis acid to 1.0 equivalent of said 1-(V)-1,3-propane diol.

12. The method of claim 11 wherein 0.5 to 2.0 equivalents of said Lewis acid is added.

13. A method for the diastereoselective preparation of compounds of Formula IV:

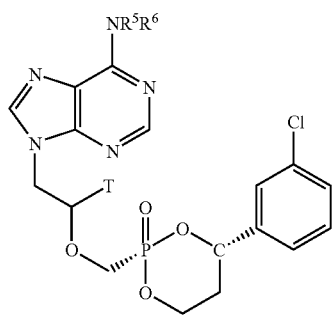

Formula IV wherein:
R$^5$ tert-butyloxycarbonyl, benzyloxycarbonyl, trifluoroacetyl or benzyl, and R$^6$ is hydrogen; or,
R$^5$ and R$^6$ taken together are phthalimidoyl, phenylmethylidene, dimethylaminomethylidene and diethylaminomethylidene;
T is selected from the group consisting of H and lower alkyl; the method comprising:
combining (R)-1-(3-chlorophenyl)-1,3-propanediol with a compound of Formula III in the presence of a Lewis acid

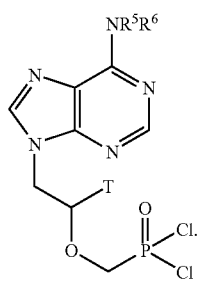

Formula III wherein the ratio of cis- to trans-diastereomers of the compounds of Formula IV formed is greater than or equal to 3:1.

14. The method of claim 13 wherein said (R)-1-(3-chlorophenyl)-1,3-propanediol is added to said Lewis acid and then the diol-Lewis acid complex is added to said compound of Formula III.

15. The method of claim 13 wherein said Lewis acid contains an element selected from the group consisting of titanium, tin, aluminum, zinc, boron, magnesium, samarium, bismuth, iron, mercury, copper, silver, and cobalt.

16. The method of claim 15 wherein said element is selected from the group consisting of titanium, boron, aluminum, tin, and samarium.

17. The method of claim 16 wherein said Lewis acid contains a group independently selected from the group consisting of alkoxy, alkyl, aryl, and an inorganic radical.

18. The method of claim 17 wherein said inorganic radical is selected from the group consisting of chloride, iodide, bromide, and fluoride.

19. The method of claim 18 wherein said Lewis acid is selected from the group consisting of TiCl$_4$, BF$_3$, SnCl$_4$, SmI$_2$, and AlCl$_3$.

20. The method of claim 19 wherein said Lewis acid is TiC$_4$.

21. The method of claim 16 wherein said Lewis acid is Ti(O-(C$_1$-C$_4$)alkyl)$_4$.

22. The method of claim 13 further comprising adding a base selected from the group consisting of tertiary alkyl amines, N-containing heterocyclic aromatic base, and non-nucleophilic inorganic bases.

23. The method of claim 22 wherein said base is selected from the group consisting of triethylamine, tri(n-butyl)amine, pyridine, quinoline, and diisopropylethylamine.

24. The method of claim 13 wherein the temperature for the reaction is between −78° C. and 60° C.

25. The method of claim 24 wherein said temperature is between −20° C. and 50° C.

26. The method of claim 25 wherein said temperature is between 15° C. and 42° C.

27. The method of claim 13 further comprising:
adding 0.01 to 5 equivalents of said Lewis acid to 1.0 equivalent of said (R)-1-(3-chlorophenyl)- 1,3-propanediol.

28. The method of claim 27 wherein 0.5 to 2.0 equivalents of said Lewis acid is added.

29. A method for the diastereoselective preparation of compounds of Formula V:

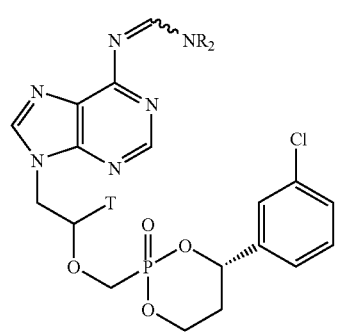

Formula V wherein:
R is lower alkyl;
T is selected from the group consisting of H and lower alkyl; the method comprising:
combining (R)-1-(3-chlorophenyl)-1,3-propanediol with said compound of Formula VI in the presence of a Lewis acid:

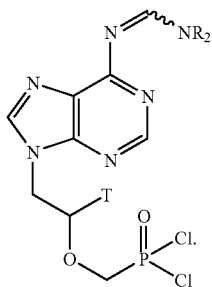

Formula VI wherein the ratio of cis- to trans-diastereomers of the compounds of Formula V formed is greater than or equal to 3:1.

30. The method of claim 29 wherein said (R)-1-(3-chlorophenyl)-1,3-propanediol is added to said Lewis acid and then the diol-Lewis acid complex is added to said compound of Formula VI.

31. The method of claim 29 wherein said Lewis acid contains an element selected from the group consisting of titanium, tin, aluminum, zinc, boron, magnesium, samarium, bismuth, iron, mercury, copper, silver, and cobalt and contains a group independently selected from the group consisting of alkoxy, alkyl, aryl, and an inorganic radical wherein said inorganic radical is selected from the group consisting of chloride, iodide, bromide, and fluoride.

32. The method of claim 31 wherein said Lewis acid is selected from the group consisting of $TiCl_4$, $BF_3$, $SnCl_4$, $SmI_2$, and $AlCl_3$.

33. The method of claim 32 wherein said Lewis acid is $TiCl_4$.

34. The method of claim 31 wherein said Lewis acid is $Ti(O-(C_1-C_4)alkyl)_4$.

35. The method of claim 29 further comprising adding a base selected from the group consisting of tertiary alkyl amines, N-containing heterocyclic aromatic base, and non-nucleophilic inorganic bases.

36. The method of claim 35 wherein said base is selected from the group consisting of triethylamine, tri(n-butyl)amine, pyridine, quinoline, and diisopropylethylamine.

37. The method of claim 29 wherein said temperature is between 15° C. and 42° C.

38. The method of claim 29 further comprising:
adding 0.01 to 5 equivalents of said Lewis acid to 1.0 equivalent of said (R)-1-(3-chlorophenyl)-1,3-propanediol.

39. The method of claim 38 wherein 0.5 to 2.0 equivalents of said Lewis acid is added.

* * * * *

UNITED STATES PATENT AND TRADEMARK OFFICE
CERTIFICATE OF CORRECTION

PATENT NO. : 7,582,758 B2 Page 1 of 1
APPLICATION NO. : 11/144348
DATED : September 1, 2009
INVENTOR(S) : Kevin V. Martin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 982 days.

Signed and Sealed this

Fourteenth Day of September, 2010

David J. Kappos
*Director of the United States Patent and Trademark Office*